United States Patent [19]

Morgan et al.

[11] Patent Number: 5,283,191
[45] Date of Patent: Feb. 1, 1994

[54] MAREKS' DISEASE VIRUS VACCINE

[75] Inventors: Robin W. Morgan, Landenberg, Pa.; Johannes A. J. Claessens, Boxmeer, Netherlands; Martha J. Willemse, Nijmegen, Netherlands; Paulus J. A. Sondermeijer, Boxmeer, Netherlands

[73] Assignee: Akzo N.V., Arnhem, Netherlands

[21] Appl. No.: 912,015

[22] Filed: Jul. 10, 1992

Related U.S. Application Data

[63] Continuation of Ser. No. 615,211, Nov. 16, 1990, abandoned.

[51] Int. Cl.$^5$ .............. C12P 21/02; C12P 19/34; C12N 15/00; C12N 7/00; C12N 5/00; C12N 1/21; C12N 1/16; C12N 1/18; C07K 3/00; C07H 15/12

[52] U.S. Cl. .............. 435/252.3; 435/252.33; 435/69.3; 435/172.3; 435/235.1; 435/320.1; 435/240.2; 435/254.21; 435/254.2; 536/23.72; 530/350; 935/9; 935/32; 935/36; 935/57; 935/63; 935/65

[58] Field of Search .............. 435/69.3, 91, 172.3, 435/235.1, 252.3, 240.2, 255, 256, 320.1; 536/27; 530/350; 935/9, 32, 36, 57, 63, 65

[56] References Cited

FOREIGN PATENT DOCUMENTS 9002803 3/1990 World Int. Prop. O. ... C12N 15/38

OTHER PUBLICATIONS

Sanbrook et al Molecular Cloning vol. 2 Cold Spring Harbor Laboratory, CSH, NY (1989) pp. 8.3-8.52 & 12.2-12.29.
Boyle et al Virus Research vol. 10 pp. 343-356 (1988).
Igrashi et al. Virology vol. 157 pp. 351-358 (1987).
Ross et al. J. Gen. Virol. vol. 70 pp. 1789-1804 (1989).
Heffman et al. Proc. Natl. Acad. Sci. USA vol. 80 pp. 31-35 (1983).
Young et al. Proc. Natl. Acad. Sci. USA vol. 80 pp. 1194-1198 (1983).
Silva et al. Virology vol. 136 pp. 307-320 (1984).
Ikuta et al. J. Gen. Virol. vol. 64 pp. 2597-2610.

*Primary Examiner*—Joan Ellis
*Attorney, Agent, or Firm*—Donna Bobrowicz

[57] ABSTRACT

The invention is concerned with the MD18 and MD20 polypeptides of Marek's Disease virus which can be used to vaccinate poultry against MD.

The invention also relates to nucleic acid sequences encoding the MD18 or MD20 polypeptides. Said sequences can be used for the preparation of a subunit or vector vaccine.

17 Claims, 3 Drawing Sheets

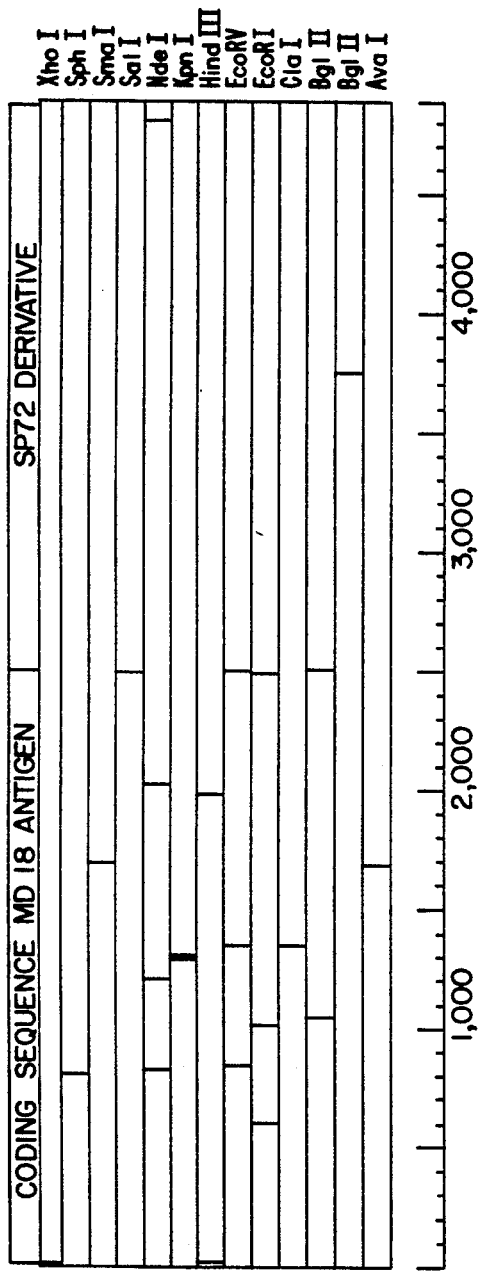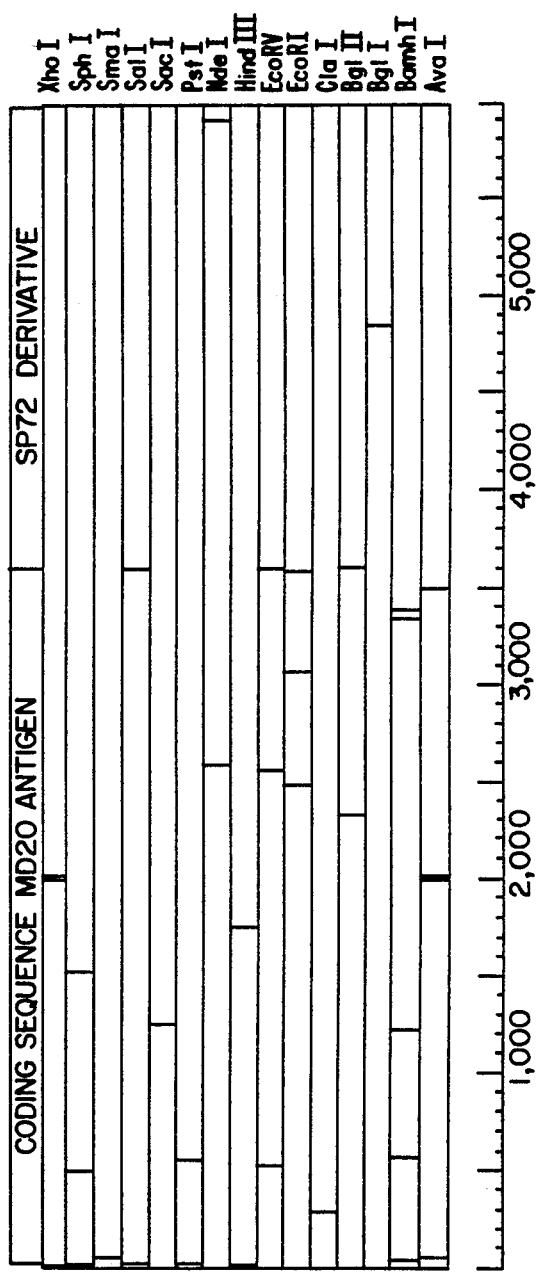
FIG. 2(A)
FIG. 2(B)

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2015 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Marek's disease herpesvirus
        ( B ) STRAIN: GA ( i x ) FEATURE:
  ( A ) NAME/KEY: CDS
  ( B ) LOCATION: 14..2005
  ( D ) OTHER INFORMATION: /label=pMD18

( x i ) SEQUENCE DESCRIPTION: SEQ ID NO:1:

```
ATTTTTATCT GAA ATG AAT CCG GCC GAC CAT CCA TCG GTG TAT GTA GCG            49
           Met Asn Pro Ala Asp His Pro Ser Val Tyr Val Ala
           1             5                   10

GGC TAT CTG GCA TTA TAT GGG GCG GAT GAA AGT GAT GAA TTG AAT ATC            97
Gly Tyr Leu Ala Leu Tyr Gly Ala Asp Glu Ser Asp Glu Leu Asn Ile
        15              20                  25

GAC CGC AAA GAT ATT CGC GCC GCG ATT CCG ACA CCA GCT CCT TTA CCA           145
Asp Arg Lys Asp Ile Arg Ala Ala Ile Pro Thr Pro Ala Pro Leu Pro
    30              35                  40

ATA AAT ATA GAT CAC AGA AGA GAT TGC ACA GTC GGA GCA GTT CTT GCG           193
Ile Asn Ile Asp His Arg Arg Asp Cys Thr Val Gly Ala Val Leu Ala
45              50                  55                      60

CTA ATA GAT GAT GAA CAT GGA TTA TTT TTC CTG GGA AAG ATA AAT TGT           241
Leu Ile Asp Asp Glu His Gly Leu Phe Phe Leu Gly Lys Ile Asn Cys
                65                  70                  75

CCT GTG ATG GTA CGT ACA CTA GAG ACA GCC GCC AGT CAA GAA ATA TTC           289
Pro Val Met Val Arg Thr Leu Glu Thr Ala Ala Ser Gln Glu Ile Phe
            80                  85                  90

AGC GAA CTT GAT AAT CTT AAA CCA GAT GAT AAA TTG CTA TAT ATA ATT           337
Ser Glu Leu Asp Asn Leu Lys Pro Asp Asp Lys Leu Leu Tyr Ile Ile
            95                  100                 105

ACA AAT TAT CTT CCA TCG GTA TCG CTG TCC TCA CGA CGC CTA GCA CCG           385
Thr Asn Tyr Leu Pro Ser Val Ser Leu Ser Ser Arg Arg Leu Ala Pro
    110                 115                 120

GGG GAA ACG GCA GAT GAG ACT TTT TTG GCA CAT GTT GCT TTG TGT TTA           433
Gly Glu Thr Ala Asp Glu Thr Phe Leu Ala His Val Ala Leu Cys Leu
125             130                 135                     140

TTG GGG AAG CGA ATT GGA ACT ATT GTT ACA TAT GAT CTC ACC CCG GAA           481
Leu Gly Lys Arg Ile Gly Thr Ile Val Thr Tyr Asp Leu Thr Pro Glu
                145                 150                 155

GAG GCT ATA GAG CCG TTC AGA AAG CTT TCT CCA AAT TCT AAA GCG ACC           529
Glu Ala Ile Glu Pro Phe Arg Lys Leu Ser Pro Asn Ser Lys Ala Thr
            160                 165                 170

TTG CTA TCA CAG GGC AAG GAA ACT GAA CGG CTC TTA GGT GAG ATG GTG           577
Leu Leu Ser Gln Gly Lys Glu Thr Glu Arg Leu Leu Gly Glu Met Val
        175                 180                 185

TGG TAT CCG AGC AAA AAT GCA ATA ACC AAA GCG TTA TTA GGA ACG GCG           625
Trp Tyr Pro Ser Lys Asn Ala Ile Thr Lys Ala Leu Leu Gly Thr Ala
190                 195                 200

GTT AAT AAT ATG TTA CTG CGA GAT AGA TGG CAA ATT ATC TCC GAA CGA           673
Val Asn Asn Met Leu Leu Arg Asp Arg Trp Gln Ile Ile Ser Glu Arg
205                 210                 215                 220

AGA CGC ATG GCT GGT ATA ACT GGA CAA AAG TAT TTG CAA GCA TCA TCT           721
Arg Arg Met Ala Gly Ile Thr Gly Gln Lys Tyr Leu Gln Ala Ser Ser
                225                 230                 235

TTT ACG GCA TTG ACC GAT TCA ATG ACG TCA AAT AAC GTG TCA GTC ACC       769
    Phe Thr Ala Leu Thr Asp Ser Met Thr Ser Asn Asn Val Ser Val Thr
                240                 245                 250

CAC CCA ATT TGT GAA AAC GCA AAC CCG GGT AAC ATA CAA AAG GAT GAG           817
His Pro Ile Cys Glu Asn Ala Asn Pro Gly Asn Ile Gln Lys Asp Glu
        255                 260                 265

GAA ATG CAA GTG TGT ATC AGT CCA GCA CAA ACG AGT GAA ACG TTA AAT           865
Glu Met Gln Val Cys Ile Ser Pro Ala Gln Thr Ser Glu Thr Leu Asn
270                 275                 280

GCT GGA GTG CTG TCT GGA TGC AAC GAT TTC CAT AGA CTT CCC CAC TCC           913
Ala Gly Val Leu Ser Gly Cys Asn Asp Phe His Arg Leu Pro His Ser
```

-continued

| | | | | | | | | | | | | | | | | |
|---|---|---|---|---|---|---|---|---|---|---|---|---|---|---|---|---|
| 285 | | | | | 290 | | | | | 295 | | | | | 300 | |
| GAC | CCT | GCA | TCA | ACG | AGC | GAT | CAA | ACC | AAT | TTG | CAA | TCG | CTA | ATA | GAA | 961 |
| Asp | Pro | Ala | Ser | Thr | Ser | Asp | Gln | Thr | Asn | Leu | Gln | Ser | Leu | Ile | Glu | |
| | | | | 305 | | | | | 310 | | | | | 315 | | |
| CCG | TCC | ATG | AAC | ACT | CAA | TCT | TCT | CGC | CCA | CCC | GGA | GAC | GAT | TTT | ATT | 1009 |
| Pro | Ser | Met | Asn | Thr | Gln | Ser | Ser | Arg | Pro | Pro | Gly | Asp | Asp | Phe | Ile | |
| | | | 320 | | | | | 325 | | | | | 330 | | | |
| TGG | GTC | CCG | ATT | AAA | AGC | TAT | AAT | CAG | CTA | GTA | TCG | AGA | AAT | GCT | TCT | 1057 |
| Trp | Val | Pro | Ile | Lys | Ser | Tyr | Asn | Gln | Leu | Val | Ser | Arg | Asn | Ala | Ser | |
| | | 335 | | | | | 340 | | | | | 345 | | | | |
| CAG | CCA | ACG | AAT | ATT | CCC | GAT | ATT | GCA | ATT | ACA | TCG | AAT | CAG | CCT | CCG | 1105 |
| Gln | Pro | Thr | Asn | Ile | Pro | Asp | Ile | Ala | Ile | Thr | Ser | Asn | Gln | Pro | Pro | |
| | 350 | | | | | 355 | | | | | 360 | | | | | |
| TTT | ATT | CCC | CCG | GCG | TTA | ATG | AAT | ACA | TCG | ATA | TCA | GGT | CAA | CAC | TCC | 1153 |
| Phe | Ile | Pro | Pro | Ala | Leu | Met | Asn | Thr | Ser | Ile | Ser | Gly | Gln | His | Ser | |
| 365 | | | | | 370 | | | | | 375 | | | | | 380 | |
| ATC | CCA | AGT | GGA | TAT | GCC | CAA | TAT | GGG | TAC | CCT | ACA | CCC | GTA | GGT | ACC | 1201 |
| Ile | Pro | Ser | Gly | Tyr | Ala | Gln | Tyr | Gly | Tyr | Pro | Thr | Pro | Val | Gly | Thr | |
| | | | | 385 | | | | | 390 | | | | | 395 | | |
| CAT | AAC | TCT | CTG | CTT | CCA | TTG | GGA | CCT | GTA | AAT | CAA | ATG | GGC | GGA | TTT | 1249 |
| His | Asn | Ser | Leu | Leu | Pro | Leu | Gly | Pro | Val | Asn | Gln | Met | Gly | Gly | Phe | |
| | | | 400 | | | | | 405 | | | | | 410 | | | |
| CAA | TAT | GGA | CCT | CAG | GTG | TAC | CCC | TTG | TCA | TAT | GGA | CAA | TCG | CCT | TTA | 1297 |
| Gln | Tyr | Gly | Pro | Gln | Val | Tyr | Pro | Leu | Ser | Tyr | Gly | Gln | Ser | Pro | Leu | |
| | | 415 | | | | | 420 | | | | | 425 | | | | |
| GAA | GCA | AAA | CTG | ACA | GCC | TTA | CTT | GAA | TGC | ATG | ACA | AAG | GAA | AAG | AGA | 1345 |
| Glu | Ala | Lys | Leu | Thr | Ala | Leu | Leu | Glu | Cys | Met | Thr | Lys | Glu | Lys | Arg | |
| | 430 | | | | | 435 | | | | | 440 | | | | | |
| CCA | GTG | GAT | GAG | GAG | CAC | AGA | GGC | GAC | GAT | ATG | CAT | ACT | ACT | AGG | GAA | 1393 |
| Pro | Val | Asp | Glu | Glu | His | Arg | Gly | Asp | Asp | Met | His | Thr | Thr | Arg | Glu | |
| 445 | | | | | 450 | | | | | 455 | | | | | 460 | |
| GAA | CGA | GGA | CGA | CGT | GGA | CGT | AAG | CGA | CCA | TAC | GAA | TTT | GAC | AGA | TCT | 1441 |
| Glu | Arg | Gly | Arg | Arg | Gly | Arg | Lys | Arg | Pro | Tyr | Glu | Phe | Asp | Arg | Ser | |
| | | | | 465 | | | | | 470 | | | | | 475 | | |
| ATC | GAG | TCT | GAT | CTT | TAT | TAT | CCC | GGT | GAA | TTC | CGT | CGG | TCT | AAT | TTT | 1489 |
| Ile | Glu | Ser | Asp | Leu | Tyr | Tyr | Pro | Gly | Glu | Phe | Arg | Arg | Ser | Asn | Phe | |
| | | | 480 | | | | | 485 | | | | | 490 | | | |
| TCT | CCT | CCT | CAA | GCC | AGT | AGT | ATG | AAA | TAT | GAA | GAA | ACT | ACT | GGG | GGT | 1537 |
| Ser | Pro | Pro | Gln | Ala | Ser | Ser | Met | Lys | Tyr | Glu | Glu | Thr | Thr | Gly | Gly | |
| | | 495 | | | | | 500 | | | | | 505 | | | | |
| CGG | CAT | GAT | CTG | AGT | CAA | ACA | GGA | CCC | GTA | TTA | AAT | AGT | CTA | ATG | GGA | 1585 |
| Arg | His | Asp | Leu | Ser | Gln | Thr | Gly | Pro | Val | Leu | Asn | Ser | Leu | Met | Gly | |
| | 510 | | | | | 515 | | | | | 520 | | | | | |
| GCT | GTG | ACT | TCC | CTA | CAA | AAA | GAA | GTC | GAA | CGG | CTA | AAT | GGA | GGA | AAT | 1633 |
| Ala | Val | Thr | Ser | Leu | Gln | Lys | Glu | Val | Glu | Arg | Leu | Asn | Gly | Gly | Asn | |
| 525 | | | | | 530 | | | | | 535 | | | | | 540 | |
| TTA | CCG | ATA | TCA | AAT | GCA | CAA | AGT | TCA | TAT | GGA | GTG | CCC | AAT | GGG | ATG | 1681 |
| Leu | Pro | Ile | Ser | Asn | Ala | Gln | Ser | Ser | Tyr | Gly | Val | Pro | Asn | Gly | Met | |
| | | | | 545 | | | | | 550 | | | | | 555 | | |
| CAT | GCC | CCA | GTT | TAT | TAC | TCA | TAC | CCT | CCT | CCG | GGA | ACA | CAT | CCC | ACA | 1729 |
| His | Ala | Pro | Val | Tyr | Tyr | Ser | Tyr | Pro | Pro | Pro | Gly | Thr | His | Pro | Thr | |
| | | | 560 | | | | | 565 | | | | | 570 | | | |
| GTT | TCA | TGG | CCC | ATG | GGA | GTC | GAA | CGC | CCT | ATG | CCT | TCC | ACG | GAA | GGA | 1777 |
| Val | Ser | Trp | Pro | Met | Gly | Val | Glu | Arg | Pro | Met | Pro | Ser | Thr | Glu | Gly | |
| | | 575 | | | | | 580 | | | | | 585 | | | | |
| AAA | ACT | TCT | ACC | AAT | TCC | ACG | GTC | ATT | CCT | GTG | CCA | GTT | TCA | GAT | CCG | 1825 |
| Lys | Thr | Ser | Thr | Asn | Ser | Thr | Val | Ile | Pro | Val | Pro | Val | Ser | Asp | Pro | |
| | 590 | | | | | 595 | | | | | 600 | | | | | |
| GAG | GCT | GGT | CGA | AAT | GTA | CCA | ATA | ACT | GCG | ACC | ATC | TCT | CAG | GAG | CGT | 1873 |
| Glu | Ala | Gly | Arg | Asn | Val | Pro | Ile | Thr | Ala | Thr | Ile | Ser | Gln | Glu | Arg | |
| 605 | | | | | 610 | | | | | 615 | | | | | 620 | |

```
TCC  GAC  GGA  ATT  CAG  AAG  GAA  AGC  ATC  GAG  CAA  TCA  CGG  GAT  ACC  ATG        1921
Ser  Asp  Gly  Ile  Gln  Lys  Glu  Ser  Ile  Glu  Gln  Ser  Arg  Asp  Thr  Met
               625                      630                      635

AAT  GCT  AGC  GCC  GTA  GCT  GGT  ATA  CAC  CGC  ACC  AGT  GAT  GCC  GGC  GTC        1969
Asn  Ala  Ser  Ala  Val  Ala  Gly  Ile  His  Arg  Thr  Ser  Asp  Ala  Gly  Val
               640                      645                      650

GAT  GTA  TTT  ATT  AAT  CAA  ATG  ATG  GCG  CAT  CAA  TAA  TACAGGGAGC                 2015
Asp  Val  Phe  Ile  Asn  Gln  Met  Met  Ala  His  Gln
               655                      660
```

( 2 ) INFORMATION FOR SEQ ID NO:2:

( i ) SEQUENCE CHARACTERISTICS:
        ( A ) LENGTH: 663 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Pro  Ala  Asp  His  Pro  Ser  Val  Tyr  Val  Ala  Gly  Tyr  Leu  Ala
 1               5                       10                      15

Leu  Tyr  Gly  Ala  Asp  Glu  Ser  Asp  Leu  Asn  Ile  Asp  Arg  Lys  Asp
               20                       25                      30

Ile  Arg  Ala  Ala  Ile  Pro  Thr  Pro  Ala  Pro  Leu  Pro  Ile  Asn  Ile  Asp
               35                       40                      45

His  Arg  Arg  Asp  Cys  Thr  Val  Gly  Ala  Val  Leu  Ala  Leu  Ile  Asp  Asp
               50                       55                      60

Glu  His  Gly  Leu  Phe  Phe  Leu  Gly  Lys  Ile  Asn  Cys  Pro  Val  Met  Val
 65                         70                       75                      80

Arg  Thr  Leu  Glu  Thr  Ala  Ala  Ser  Gln  Glu  Ile  Phe  Ser  Glu  Leu  Asp
                    85                       90                      95

Asn  Leu  Lys  Pro  Asp  Asp  Lys  Leu  Leu  Tyr  Ile  Ile  Thr  Asn  Tyr  Leu
               100                      105                     110

Pro  Ser  Val  Ser  Leu  Ser  Ser  Arg  Arg  Leu  Ala  Pro  Gly  Glu  Thr  Ala
               115                      120                     125

Asp  Glu  Thr  Phe  Leu  Ala  His  Val  Ala  Leu  Cys  Leu  Leu  Gly  Lys  Arg
               130                      135                     140

Ile  Gly  Thr  Ile  Val  Thr  Tyr  Asp  Leu  Thr  Pro  Glu  Glu  Ala  Ile  Glu
145                      150                      155                     160

Pro  Phe  Arg  Lys  Leu  Ser  Pro  Asn  Ser  Lys  Ala  Thr  Leu  Leu  Ser  Gln
               165                      170                     175

Gly  Lys  Glu  Thr  Glu  Arg  Leu  Leu  Gly  Glu  Met  Val  Trp  Tyr  Pro  Ser
               180                      185                     190

Lys  Asn  Ala  Ile  Thr  Lys  Ala  Leu  Leu  Gly  Thr  Ala  Val  Asn  Asn  Met
               195                      200                     205

Leu  Leu  Arg  Asp  Arg  Trp  Gln  Ile  Ile  Ser  Glu  Arg  Arg  Arg  Met  Ala
210                      215                      220

Gly  Ile  Thr  Gly  Gln  Lys  Tyr  Leu  Gln  Ala  Ser  Ser  Phe  Thr  Ala  Leu
225                      230                      235                     240

Thr  Asp  Ser  Met  Thr  Ser  Asn  Asn  Val  Ser  Val  Thr  His  Pro  Ile  Cys
               245                      250                     255

Glu  Asn  Ala  Asn  Pro  Gly  Asn  Ile  Gln  Lys  Asp  Glu  Glu  Met  Gln  Val
               260                      265                     270

Cys  Ile  Ser  Pro  Ala  Gln  Thr  Ser  Glu  Thr  Leu  Asn  Ala  Gly  Val  Leu
               275                      280                     285

Ser  Gly  Cys  Asn  Asp  Phe  His  Arg  Leu  Pro  His  Ser  Asp  Pro  Ala  Ser
               290                      295                     300

Thr  Ser  Asp  Gln  Thr  Asn  Leu  Gln  Ser  Leu  Ile  Glu  Pro  Ser  Met  Asn
```

```
305                   310                   315                   320
Thr Gln Ser Ser Arg Pro Pro Gly Asp Asp Phe Ile Trp Val Pro Ile
                325                 330                 335
Lys Ser Tyr Asn Gln Leu Val Ser Arg Asn Ala Ser Gln Pro Thr Asn
                340                 345                 350
Ile Pro Asp Ile Ala Ile Thr Ser Asn Gln Pro Pro Phe Ile Pro Pro
                355                 360                 365
Ala Leu Met Asn Thr Ser Ile Ser Gly Gln His Ser Ile Pro Ser Gly
            370                 375                 380
 Tyr Ala Gln Tyr Gly Tyr Pro Thr Pro Val Gly Thr His Asn Ser Leu
385                 390                 395                 400
Leu Pro Leu Gly Pro Val Asn Gln Met Gly Gly Phe Gln Tyr Gly Pro
                405                 410                 415
Gln Val Tyr Pro Leu Ser Tyr Gly Gln Ser Pro Leu Glu Ala Lys Leu
                420                 425                 430
Thr Ala Leu Leu Glu Cys Met Thr Lys Glu Lys Arg Pro Val Asp Glu
            435                 440                 445
Glu His Arg Gly Asp Asp Met His Thr Thr Arg Glu Glu Arg Gly Arg
        450                 455                 460
Arg Gly Arg Lys Arg Pro Tyr Glu Phe Asp Arg Ser Ile Glu Ser Asp
465                 470                 475                 480
Leu Tyr Tyr Pro Gly Glu Phe Arg Arg Ser Asn Phe Ser Pro Pro Gln
                485                 490                 495
Ala Ser Ser Met Lys Tyr Glu Glu Thr Thr Gly Gly Arg His Asp Leu
                500                 505                 510
Ser Gln Thr Gly Pro Val Leu Asn Ser Leu Met Gly Ala Val Thr Ser
            515                 520                 525
Leu Gln Lys Glu Val Glu Arg Leu Asn Gly Gly Asn Leu Pro Ile Ser
        530                 535                 540
Asn Ala Gln Ser Ser Tyr Gly Val Pro Asn Gly Met His Ala Pro Val
545                 550                 555                 560
Tyr Tyr Ser Tyr Pro Pro Gly Thr His Pro Thr Val Ser Trp Pro
                565                 570                 575
Met Gly Val Glu Arg Pro Met Pro Ser Thr Glu Gly Lys Thr Ser Thr
            580                 585                 590
Asn Ser Thr Val Ile Pro Val Pro Val Ser Asp Pro Glu Ala Gly Arg
        595                 600                 605
Asn Val Pro Ile Thr Ala Thr Ile Ser Gln Glu Arg Ser Asp Gly Ile
    610                 615                 620
Gln Lys Glu Ser Ile Glu Gln Ser Arg Asp Thr Met Asn Ala Ser Ala
625                 630                 635                 640
Val Ala Gly Ile His Arg Thr Ser Asp Ala Gly Val Asp Val Phe Ile
                645                 650                 655
Asn Gln Met Met Ala His Gln
                660
```

(2) INFORMATION FOR SEQ ID NO:3:

(i) SEQUENCE CHARACTERISTICS:
        (A) LENGTH: 3265 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Marek's disease herpesvirus
        (B) STRAIN: GA ( i x ) FEATURE:
    ( A ) NAME/KEY: CDS
    ( B ) LOCATION: 41..3265
    ( D ) OTHER INFORMATION: /label=pMD20

( x i ) SEQUENCE DESCRIPTION: SEQ ID NO:3:

```
GAGTCTTCTG TAGTCGTATG TTCTTGAGCT GGTTTGCATT ATG GCG AGA TTT TCG        55
                                             Met Ala Arg Phe Ser
                                              1               5

TCT ATA TCC GAT ACG CTC GAA AGT GAT GAC TCG GGA ATT AAG GTC TTA       103
Ser Ile Ser Asp Thr Leu Glu Ser Asp Asp Ser Gly Ile Lys Val Leu
             10              15                  20

TTT GCC GTA GAT GGT TGT GCC GTG TCG TTT TCC CTG GCC CTT CTT ACA       151
Phe Ala Val Asp Gly Cys Ala Val Ser Phe Ser Leu Ala Leu Leu Thr
         25              30                  35

GGT CAG ATA CCC TCT ACT AAC TCC GTT TAT GTT ATC GGC TAT TGG GAT       199
Gly Gln Ile Pro Ser Thr Asn Ser Val Tyr Val Ile Gly Tyr Trp Asp
         40              45                  50

CCA AGC GAC CGA TTT TCA AGC ATA CCC TTT CTC GAC GGG GAT CCT AAT       247
Pro Ser Asp Arg Phe Ser Ser Ile Pro Phe Leu Asp Gly Asp Pro Asn
         55              60                  65

ACT AAT GAG AGA ATA TCT ACC ACC GTT TGT AAT TTA GAG GAT GTT CCC       295
Thr Asn Glu Arg Ile Ser Thr Thr Val Cys Asn Leu Glu Asp Val Pro
 70              75                  80                      85

AGC CCT CTA AGA GTA GAA TTT TGT CTT CTG AAC CAA ATG GCA TCA GGT       343
Ser Pro Leu Arg Val Glu Phe Cys Leu Leu Asn Gln Met Ala Ser Gly
             90                  95                 100

ATG GGC GGT GCT GAT TTA AAA CTG AGA ACA CGT GCA ATA TTC GTA TGC       391
Met Gly Gly Ala Asp Leu Lys Leu Arg Thr Arg Ala Ile Phe Val Cys
            105              110                 115

CGA TTT ACA TCA TGG TCC GAA ATG AAC GCT ATC GCA AAT TCA ATA ATT       439
Arg Phe Thr Ser Trp Ser Glu Met Asn Ala Ile Ala Asn Ser Ile Ile
        120              125                 130

TAT GGA ACG CCA ATT CAA GCC GGT GTT TTA CAA GCA ACA ATA TCT GAA       487
Tyr Gly Thr Pro Ile Gln Ala Gly Val Leu Gln Ala Thr Ile Ser Glu
        135              140                 145

ACT GAA ACG TTC ATG TTA CAT GAT GAA TTC AAC CTT GCT CTT CAC GTC   535
    Thr Glu Thr Phe Met Leu His Asp Glu Phe Asn Leu Ala Leu His Val
    150              155                 160                 165

TTT CTC AAT GGG TTA TCT CTG AAG GGT CGT AAC AAA AAA GAT GTT TGT       583
Phe Leu Asn Gly Leu Ser Leu Lys Gly Arg Asn Lys Lys Asp Val Cys
            170              175                 180

ATG TCA TTG AAT CAC AAT TAT ATA TCG AGC GTA TCT GAG AAT TTC CCA       631
Met Ser Leu Asn His Asn Tyr Ile Ser Ser Val Ser Glu Asn Phe Pro
            185              190                 195

AGG GGT AAA CGA GGT CTG ACT GGA CTC TAT TTA CAA CAC GAA CAA AAG       679
Arg Gly Lys Arg Gly Leu Thr Gly Leu Tyr Leu Gln His Glu Gln Lys
            200              205                 210

GTC ACA GCA GCA TAT CGG CGT ATA TAT GGT GGA TCT ACT ACA ACT GCT       727
Val Thr Ala Ala Tyr Arg Arg Ile Tyr Gly Gly Ser Thr Thr Thr Ala
215              220                 225

TTT TGG TAC GTG TCC AAA TTC GGA CCA GAT GAA AAA AGT CTT GTT TTG       775
Phe Trp Tyr Val Ser Lys Phe Gly Pro Asp Glu Lys Ser Leu Val Leu
230              235                 240                 245

GCC CTA CGT TAT TAC CTT TTG CAG GCA CAG GAA GAA GTT ACT GGT ATT       823
Ala Leu Arg Tyr Tyr Leu Leu Gln Ala Gln Glu Glu Val Thr Gly Ile
                 250                 255                 260

GCA ACA GGC TAT GAT CTG CAA GCC ATA AAA GAT ATA TGC AAA ACA TAC       871
Ala Thr Gly Tyr Asp Leu Gln Ala Ile Lys Asp Ile Cys Lys Thr Tyr
            265                 270                 275

GCA GTG TCG GTA AAT CCC AAT CCC ACG GGA TTT TTG GCT GCC GAT TTA       919
```

-continued

| | | | | | | | | | | | | | | |
|---|---|---|---|---|---|---|---|---|---|---|---|---|---|---|
| Ala | Val | Ser | Val | Asn | Pro | Asn | Pro | Thr | Gly | Phe | Leu | Ala | Ala | Asp | Leu |
| | | 280 | | | | 285 | | | | | 290 | | | | |

| ACG | TCA | TTT | AGT | AGA | TTA | TCA | CGT | TTT | TGT | TGT | TTA | AGT | TAC | TAT | TCC | 967 |
|---|---|---|---|---|---|---|---|---|---|---|---|---|---|---|---|---|
| Thr | Ser | Phe | Ser | Arg | Leu | Ser | Arg | Phe | Cys | Cys | Leu | Ser | Tyr | Tyr | Ser | |
| | 295 | | | | 300 | | | | | 305 | | | | | | |

| AAA | GGC | TCT | GTG | GCC | ATA | GCA | TTT | CCA | TCA | TAT | GTG | GAA | CGC | AGG | ATT | 1015 |
|---|---|---|---|---|---|---|---|---|---|---|---|---|---|---|---|---|
| Lys | Gly | Ser | Val | Ala | Ile | Ala | Phe | Pro | Ser | Tyr | Val | Glu | Arg | Arg | Ile | |
| 310 | | | | | 315 | | | | | 320 | | | | | 325 | |

| ATG | GCC | GAT | ATC | GCA | GAA | GTG | GAT | GCA | TTG | AGA | GAA | TAT | ATA | GAA | AGA | 1063 |
|---|---|---|---|---|---|---|---|---|---|---|---|---|---|---|---|---|
| Met | Ala | Asp | Ile | Ala | Glu | Val | Asp | Ala | Leu | Arg | Glu | Tyr | Ile | Glu | Arg | |
| | | | | 330 | | | | | 335 | | | | | 340 | | |

| GAC | AGA | CCC | AGT | TTG | AAG | ATT | TCG | GAT | TTG | GAA | TTC | GTT | AAA | TAT | ATA | 1111 |
|---|---|---|---|---|---|---|---|---|---|---|---|---|---|---|---|---|
| Asp | Arg | Pro | Ser | Leu | Lys | Ile | Ser | Asp | Leu | Glu | Phe | Val | Lys | Tyr | Ile | |
| | | | 345 | | | | | 350 | | | | | 355 | | | |

| TAT | TTA | GCT | TAT | TTT | GAA | TGT | TAT | AAC | CGC | GAA | CAG | TTA | AAA | CGA | CAT | 1159 |
|---|---|---|---|---|---|---|---|---|---|---|---|---|---|---|---|---|
| Tyr | Leu | Ala | Tyr | Phe | Glu | Cys | Tyr | Asn | Arg | Glu | Gln | Leu | Lys | Arg | His | |
| | | 360 | | | | | 365 | | | | | 370 | | | | |

| TTG | AAA | GAT | GTG | ACA | GTA | AGT | TTG | CCC | GAT | GAA | GAC | ATT | TAC | AAG | AAG | 1207 |
|---|---|---|---|---|---|---|---|---|---|---|---|---|---|---|---|---|
| Leu | Lys | Asp | Val | Thr | Val | Ser | Leu | Pro | Asp | Glu | Asp | Ile | Tyr | Lys | Lys | |
| | 375 | | | | | 380 | | | | | 385 | | | | | |

| TCT | TCA | CTA | GGC | AAG | TGT | GCA | GTA | GAA | AAT | TTT | TTT | ACA | CAT | GTG | AGA | 1255 |
|---|---|---|---|---|---|---|---|---|---|---|---|---|---|---|---|---|
| Ser | Ser | Leu | Gly | Lys | Cys | Ala | Val | Glu | Asn | Phe | Phe | Thr | His | Val | Arg | |
| 390 | | | | | 395 | | | | | 400 | | | | | 405 | |

| TCT | AGA | TTG | AAC | GTG | AAT | GAC | CAC | ATA | GCC | CAT | AAT | GTA | TTG | CCC | GAA | 1303 |
|---|---|---|---|---|---|---|---|---|---|---|---|---|---|---|---|---|
| Ser | Arg | Leu | Asn | Val | Asn | Asp | His | Ile | Ala | His | Asn | Val | Leu | Pro | Glu | |
| | | | | 410 | | | | | 415 | | | | | 420 | | |

| CAA | GTA | GAA | ATG | GGA | AAT | AAG | CTA | GTC | CGA | AAG | TTT | GGA | CGT | GCC | AGA | 1351 |
|---|---|---|---|---|---|---|---|---|---|---|---|---|---|---|---|---|
| Gln | Val | Glu | Met | Gly | Asn | Lys | Leu | Val | Arg | Lys | Phe | Gly | Arg | Ala | Arg | |
| | | | 425 | | | | | 430 | | | | | 435 | | | |

| ATG | TAT | CTG | TCA | ACT | ACG | ATG | ACT | AAC | GAG | TCG | CAC | TTC | ACT | GGA | ATA | 1399 |
|---|---|---|---|---|---|---|---|---|---|---|---|---|---|---|---|---|
| Met | Tyr | Leu | Ser | Thr | Thr | Met | Thr | Asn | Glu | Ser | His | Phe | Thr | Gly | Ile | |
| | | | 440 | | | | | 445 | | | | | 450 | | | |

| TGT | GAA | TGT | GCA | TCT | GTG | ATT | TTA | AAG | CGA | CTG | GAC | ACT | CTA | GAA | ATG | 1447 |
|---|---|---|---|---|---|---|---|---|---|---|---|---|---|---|---|---|
| Cys | Glu | Cys | Ala | Ser | Val | Ile | Leu | Lys | Arg | Leu | Asp | Thr | Leu | Glu | Met | |
| | 455 | | | | | 460 | | | | | 465 | | | | | |

| AAA | TTG | CAA | AAG | TAT | GGT | TGG | CCG | TCT | GAT | CGT | GTG | GAT | GGT | TCC | AAT | 1495 |
|---|---|---|---|---|---|---|---|---|---|---|---|---|---|---|---|---|
| Lys | Leu | Gln | Lys | Tyr | Gly | Trp | Pro | Ser | Asp | Arg | Val | Asp | Gly | Ser | Asn | |
| 470 | | | | | 475 | | | | | 480 | | | | | 485 | |

| CTA | ATG | GCC | GAT | AAT | CAG | AAC | AAC | TCT | ACT | TTA | ATA | CCG | TAT | GAT | AAA | 1543 |
|---|---|---|---|---|---|---|---|---|---|---|---|---|---|---|---|---|
| Leu | Met | Ala | Asp | Asn | Gln | Asn | Asn | Ser | Thr | Leu | Ile | Pro | Tyr | Asp | Lys | |
| | | | | 490 | | | | | 495 | | | | | 500 | | |

| TCT | AGG | TCT | TCT | GGA | ATG | ATA | CTC | GAG | TGT | TCG | AAC | ACT | CAT | TCT | CGA | 1591 |
|---|---|---|---|---|---|---|---|---|---|---|---|---|---|---|---|---|
| Ser | Arg | Ser | Ser | Gly | Met | Ile | Leu | Glu | Cys | Ser | Asn | Thr | His | Ser | Arg | |
| | | | 505 | | | | | 510 | | | | | 515 | | | |

| GGG | GGG | CCG | ATG | ATA | GTT | AAA | AGG | TTA | TTA | GCT | TTA | GTA | TCT | GCC | GAT | 1639 |
|---|---|---|---|---|---|---|---|---|---|---|---|---|---|---|---|---|
| Gly | Gly | Pro | Met | Ile | Val | Lys | Arg | Leu | Leu | Ala | Leu | Val | Ser | Ala | Asp | |
| | | 520 | | | | | 525 | | | | | 530 | | | | |

| TCT | CGC | GCA | GGG | GGA | ATC | GGC | CCA | GCT | AAC | ATG | CTC | ATG | GGG | ATT | GAC | 1687 |
|---|---|---|---|---|---|---|---|---|---|---|---|---|---|---|---|---|
| Ser | Arg | Ala | Gly | Gly | Ile | Gly | Pro | Ala | Asn | Met | Leu | Met | Gly | Ile | Asp | |
| | 535 | | | | | 540 | | | | | 545 | | | | | |

| TCT | GCA | ATA | GAT | GGA | CCC | CTT | CCA | GTT | TAC | CGT | GTG | GGC | ATG | TCA | AAG | 1735 |
|---|---|---|---|---|---|---|---|---|---|---|---|---|---|---|---|---|
| Ser | Ala | Ile | Asp | Gly | Pro | Leu | Pro | Val | Tyr | Arg | Val | Gly | Met | Ser | Lys | |
| 550 | | | | | 555 | | | | | 560 | | | | | 565 | |

| GGC | AGA | CAG | GCT | TTT | ACG | GTG | CTT | ATG | ACC | GAA | TGT | TGG | GAA | AGG | ACC | 1783 |
|---|---|---|---|---|---|---|---|---|---|---|---|---|---|---|---|---|
| Gly | Arg | Gln | Ala | Phe | Thr | Val | Leu | Met | Thr | Glu | Cys | Trp | Glu | Arg | Thr | |
| | | | | 570 | | | | | 575 | | | | | 580 | | |

| ATT | CCA | TCT | CCG | GGA | AGT | GCG | AAA | GCG | CAT | TTG | ATC | AAG | CTT | AAC | AAC | 1831 |
|---|---|---|---|---|---|---|---|---|---|---|---|---|---|---|---|---|
| Ile | Pro | Ser | Pro | Gly | Ser | Ala | Lys | Ala | His | Leu | Ile | Lys | Leu | Asn | Asn | |
| | | | 585 | | | | | 590 | | | | | 595 | | | |

| TCT | TAC | GGT | ACT | TCG | ACA | GAA | GAC | TTG | ATT | TCA | CGA | GAC | TTA | TTC | CTA | 1879 |
|---|---|---|---|---|---|---|---|---|---|---|---|---|---|---|---|---|
| Ser | Tyr | Gly | Thr | Ser | Thr | Glu | Asp | Leu | Ile | Ser | Arg | Asp | Leu | Phe | Leu | |
| | | | | 600 | | | | | 605 | | | | | 610 | | |

| | | | | | | | | | | | | | | | | |
|---|---|---|---|---|---|---|---|---|---|---|---|---|---|---|---|---|
| ACT | TCT | GAA | ATC | GAA | CAG | CTT | ATC | GGA | AGC | ACA | GTA | GAA | TTG | CCG | GAG | 1927 |
| Thr | Ser | Glu | Ile | Glu | Gln | Leu | Ile | Gly | Ser | Thr | Val | Glu | Leu | Pro | Glu | |
| | 615 | | | | 620 | | | | | 625 | | | | | | |
| ATT | ACA | TGT | GGC | TCT | GCC | GAT | GAA | CAG | CAA | TAT | ATA | AAC | CGC | AAT | GAA | 1975 |
| Ile | Thr | Cys | Gly | Ser | Ala | Asp | Glu | Gln | Gln | Tyr | Ile | Asn | Arg | Asn | Glu | |
| 630 | | | | | 635 | | | | | 640 | | | | | 645 | |
| GTC | TTT | AAT | GGG | AAT | CTT | GCG | ATA | GGA | AAT | ATA | GTT | TTA | GAT | GTG | GAT | 2023 |
| Val | Phe | Asn | Gly | Asn | Leu | Ala | Ile | Gly | Asn | Ile | Val | Leu | Asp | Val | Asp | |
| | | | | 650 | | | | | 655 | | | | | 660 | | |
| ATA | CAT | TTA | AGA | AAC | CCC | ATA | CCT | CTT | AGA | CTT | ATG | CAT | GCA | GCG | ATA | 2071 |
| Ile | His | Leu | Arg | Asn | Pro | Ile | Pro | Leu | Arg | Leu | Met | His | Ala | Ala | Ile | |
| | | | 665 | | | | | 670 | | | | | 675 | | | |
| CGA | GGT | TTT | AGA | AGT | GGT | ATA | CTC | AGA | GCT | TTG | GCC | TTA | TTG | CTA | CCA | 2119 |
| Arg | Gly | Phe | Arg | Ser | Gly | Ile | Leu | Arg | Ala | Leu | Ala | Leu | Leu | Leu | Pro | |
| | | 680 | | | | | 685 | | | | | 690 | | | | |
| AAG | GCA | AAT | ATC | GAC | CAT | GGC | TCA | TAC | CCG | TGT | TAC | TTT | TAT | AAG | AGT | 2167 |
| Lys | Ala | Asn | Ile | Asp | His | Gly | Ser | Tyr | Pro | Cys | Tyr | Phe | Tyr | Lys | Ser | |
| | 695 | | | | | 700 | | | | | 705 | | | | | |
| TCG | TGC | AAG | AAA | TCT | AGA | GTA | ATG | GGG | GGA | GCG | CCT | TGG | ATG | CTC | CAT | 2215 |
| Ser | Cys | Lys | Lys | Ser | Arg | Val | Met | Gly | Gly | Ala | Pro | Trp | Met | Leu | His | |
| 710 | | | | | 715 | | | | | 720 | | | | | 725 | |
| GAT | GCA | GAA | CTT | GCC | CCA | GAT | TAT | TCG | ATG | TTT | GAA | AAT | GCG | GAG | TTT | 2263 |
| Asp | Ala | Glu | Leu | Ala | Pro | Asp | Tyr | Ser | Met | Phe | Glu | Asn | Ala | Glu | Phe | |
| | | | | 730 | | | | | 735 | | | | | 740 | | |
| GAT | TTA | GAA | ATG | GGC | ATA | GAT | GAC | CCT | TTA | CTC | ATA | GAC | CAA | ATA | GAT | 2311 |
| Asp | Leu | Glu | Met | Gly | Ile | Asp | Asp | Pro | Leu | Leu | Ile | Asp | Gln | Ile | Asp | |
| | | | 745 | | | | | 750 | | | | | 755 | | | |
| GAA | TCT | CTT | ACT | AGA | TGG | AGC | TCA | GAA | TCA | TCA | AGG | AGT | GTC | GAT | TTG | 2359 |
| Glu | Ser | Leu | Thr | Arg | Trp | Ser | Ser | Glu | Ser | Ser | Arg | Ser | Val | Asp | Leu | |
| | | 760 | | | | | 765 | | | | | 770 | | | | |
| GAT | CCA | GAT | AAG | CCA | TGC | GGT | TGC | CAT | GAT | AAA | ATC | GGA | TTG | AGG | GTT | 2407 |
| Asp | Pro | Asp | Lys | Pro | Cys | Gly | Cys | His | Asp | Lys | Ile | Gly | Leu | Arg | Val | |
| | 775 | | | | | 780 | | | | | 785 | | | | | |
| TGC | ATT | CCA | GTA | CCC | TCT | CCA | TAT | TTA | CTT | GTG | GGT | AGC | AAG | ACA | TTG | 2455 |
| Cys | Ile | Pro | Val | Pro | Ser | Pro | Tyr | Leu | Leu | Val | Gly | Ser | Lys | Thr | Leu | |
| 790 | | | | | 795 | | | | | 800 | | | | | 805 | |
| GCC | GGA | TTG | TCT | CGA | ATC | ATT | CAA | CAA | GCC | GTC | CTC | TTA | GAG | CGC | AAT | 2503 |
| Ala | Gly | Leu | Ser | Arg | Ile | Ile | Gln | Gln | Ala | Val | Leu | Leu | Glu | Arg | Asn | |
| | | | | 810 | | | | | 815 | | | | | 820 | | |
| TTT | GTA | GAA | ACT | ATA | GGG | CCA | TAT | CTG | AAA | AAT | TAT | GAG | ATA | ATT | GAT | 2551 |
| Phe | Val | Glu | Thr | Ile | Gly | Pro | Tyr | Leu | Lys | Asn | Tyr | Glu | Ile | Ile | Asp | |
| | | | 825 | | | | | 830 | | | | | 835 | | | |
| AGT | GGC | GTA | TAT | GGT | CAT | GGG | CGT | AGC | TTA | CGT | CTG | CCG | TTT | TTT | GGC | 2599 |
| Ser | Gly | Val | Tyr | Gly | His | Gly | Arg | Ser | Leu | Arg | Leu | Pro | Phe | Phe | Gly | |
| | | 840 | | | | | 845 | | | | | 850 | | | | |
| AAA | ATT | GAT | GAA | AAC | GGT | ATC | GTG | TCT | AGA | AGA | CTT | GTA | CCG | TTT | TTC | 2647 |
| Lys | Ile | Asp | Glu | Asn | Gly | Ile | Val | Ser | Arg | Arg | Leu | Val | Pro | Phe | Phe | |
| | 855 | | | | | 860 | | | | | 865 | | | | | |
| GTG | ATA | CCA | GAT | GAT | TGT | GCT | GAC | ATG | GAG | AAG | TTT | ATT | GTG | GCC | CAT | 2695 |
| Val | Ile | Pro | Asp | Asp | Cys | Ala | Asp | Met | Glu | Lys | Phe | Ile | Val | Ala | His | |
| 870 | | | | | 875 | | | | | 880 | | | | | 885 | |
| TTC | GAA | CCT | AAA | AAC | TTC | CAT | TTT | CAC | AGC | TCT | ATC | CCG | CTA | GAA | AAG | 2743 |
| Phe | Glu | Pro | Lys | Asn | Phe | His | Phe | His | Ser | Ser | Ile | Pro | Leu | Glu | Lys | |
| | | | | 890 | | | | | 895 | | | | | 900 | | |
| GCC | GCC | ATA | ATT | CTG | AAA | GAT | ATA | GGT | GGC | GAA | TAT | GCA | GGT | TTC | TTC | 2791 |
| Ala | Ala | Ile | Ile | Leu | Lys | Asp | Ile | Gly | Gly | Glu | Tyr | Ala | Gly | Phe | Phe | |
| | | | 905 | | | | | 910 | | | | | 915 | | | |
| GAA | AGA | AAA | ATT | ACA | GTA | AAT | AGA | GAT | ATA | TTT | TTC | GGG | ACT | CGA | TTA | 2839 |
| Glu | Arg | Lys | Ile | Thr | Val | Asn | Arg | Asp | Ile | Phe | Phe | Gly | Thr | Arg | Leu | |
| | | 920 | | | | | 925 | | | | | 930 | | | | |
| TCT | TTA | TCA | ATA | GCT | CTC | AGG | GAA | AGG | GGG | GTA | GAT | ATA | AAT | GAT | TGT | 2887 |

|     |     |     |     |     |     |     |     |     |     |     |     |     |     |     |      |
| --- | --- | --- | --- | --- | --- | --- | --- | --- | --- | --- | --- | --- | --- | --- | ---- |
| Ser | Leu | Ser | Ile | Ala | Leu | Arg | Glu | Arg | Gly | Val | Asp | Ile | Asn | Asp | Cys  |
|     |     | 935 |     |     |     | 940 |     |     |     | 945 |     |     |     |     |      |
| GCT | GCC | ATT | ACA | ACA | TTT | GTA | ACA | GAT | CAC | ATT | TTA | GAT | GAT | ATT | ATA  | 2935 |
| Ala | Ala | Ile | Thr | Thr | Phe | Val | Thr | Asp | His | Ile | Leu | Asp | Asp | Ile | Ile  |
| 950 |     |     |     |     | 955 |     |     |     | 960 |     |     |     |     | 965 |      |
| ACA | TAC | GTA | TAT | GAG | CAT | ATA | CCA | GAT | CAC | GCA | ATC | GAA | TAT | CAA | AAT  | 2983 |
| Thr | Tyr | Val | Tyr | Glu | His | Ile | Pro | Asp | His | Ala | Ile | Glu | Tyr | Gln | Asn  |
|     |     |     |     | 970 |     |     |     |     | 975 |     |     |     |     | 980 |      |
| CTT | TCT | GTC | TCG | TGT | TGT | GTT | GTC | AAA | TCG | GAT | TGG | ATC | CTG | CTG | CAG  | 3031 |
| Leu | Ser | Val | Ser | Cys | Cys | Val | Val | Lys | Ser | Asp | Trp | Ile | Leu | Leu | Gln  |
|     |     |     | 985 |     |     |     |     | 990 |     |     |     |     | 995 |     |      |
| CTA | ATC | CCC | AAT | AAA | ACA | ATA | GGA | TAT | CGT | CAC | GGG | TTT | ACA | TGT | GTG  | 3079 |
| Leu | Ile | Pro | Asn | Lys | Thr | Ile | Gly | Tyr | Arg | His | Gly | Phe | Thr | Cys | Val  |
|     |     | 1000|     |     |     |     | 1005|     |     |     |     | 1010|     |     |      |
| AGA | TTT | AAG | CAT | GCA | AGA | GCA | AGG | CGA | GCG | AGT | GCA | CGT | TCT | TAT | TTG  | 3127 |
| Arg | Phe | Lys | His | Ala | Arg | Ala | Arg | Arg | Ala | Ser | Ala | Arg | Ser | Tyr | Leu  |
|     |     | 1015|     |     |     |     | 1020|     |     |     |     | 1025|     |     |      |
| GCT | CTG | AAC | GTC | GAT | GCG | CAT | GGT | AGG | TTG | TGC | GTA | TGT | GTA | ATT | CAA  | 3175 |
| Ala | Leu | Asn | Val | Asp | Ala | His | Gly | Arg | Leu | Cys | Val | Cys | Val | Ile | Gln  |
| 1030|     |     |     |     | 1035|     |     |     |     | 1040|     |     |     |     | 1045 |
| CAG | TGT | TTT | GCG | GCC | AAG | TGC | GGA | AAT | AAT | AAA | CTT | CGC | ACA | CTT | TTC  | 3223 |
| Gln | Cys | Phe | Ala | Ala | Lys | Cys | Gly | Asn | Asn | Lys | Leu | Arg | Thr | Leu | Phe  |
|     |     |     |     | 1050|     |     |     |     | 1055|     |     |     |     | 1060|      |
| ACG | GTA | GAT | ATT | GAC | TCG | AAA | TGT | CGA | TTA | GAA | CAT | CAA | TAG |     |      | 3265 |
| Thr | Val | Asp | Ile | Asp | Ser | Lys | Cys | Arg | Leu | Glu | His | Gln |     |     |      |
|     |     |     | 1065|     |     |     |     | 1070|     |     |     |     |     |     |      |

( 2 ) INFORMATION FOR SEQ ID NO:4:

( i ) SEQUENCE CHARACTERISTICS:
        ( A ) LENGTH: 1074 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ala | Arg | Phe | Ser | Ser | Ile | Ser | Asp | Thr | Leu | Glu | Ser | Asp | Asp | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gly | Ile | Lys | Val | Leu | Phe | Ala | Val | Asp | Gly | Cys | Ala | Val | Ser | Phe | Ser |
|     |     |     |     | 20  |     |     |     |     | 25  |     |     |     |     | 30  |     |
| Leu | Ala | Leu | Leu | Thr | Gly | Gln | Ile | Pro | Ser | Thr | Asn | Ser | Val | Tyr | Val |
|     |     |     | 35  |     |     |     |     | 40  |     |     |     |     | 45  |     |     |
| Ile | Gly | Tyr | Trp | Asp | Pro | Ser | Asp | Arg | Phe | Ser | Ser | Ile | Pro | Phe | Leu |
|     | 50  |     |     |     |     | 55  |     |     |     |     | 60  |     |     |     |     |
| Asp | Gly | Asp | Pro | Asn | Thr | Asn | Glu | Arg | Ile | Ser | Thr | Thr | Val | Cys | Asn |
| 65  |     |     |     |     | 70  |     |     |     |     | 75  |     |     |     |     | 80  |
| Leu | Glu | Asp | Val | Pro | Ser | Pro | Leu | Arg | Val | Glu | Phe | Cys | Leu | Leu | Asn |
|     |     |     |     | 85  |     |     |     |     | 90  |     |     |     |     | 95  |     |
| Gln | Met | Ala | Ser | Gly | Met | Gly | Gly | Ala | Asp | Leu | Lys | Leu | Arg | Thr | Arg |
|     |     |     | 100 |     |     |     |     | 105 |     |     |     |     | 110 |     |     |
| Ala | Ile | Phe | Val | Cys | Arg | Phe | Thr | Ser | Trp | Ser | Glu | Met | Asn | Ala | Ile |
|     |     | 115 |     |     |     |     | 120 |     |     |     |     | 125 |     |     |     |
| Ala | Asn | Ser | Ile | Ile | Tyr | Gly | Thr | Pro | Ile | Gln | Ala | Gly | Val | Leu | Gln |
|     | 130 |     |     |     |     | 135 |     |     |     |     | 140 |     |     |     |     |
| Ala | Thr | Ile | Ser | Glu | Thr | Glu | Thr | Phe | Met | Leu | His | Asp | Glu | Phe | Asn |
| 145 |     |     |     |     | 150 |     |     |     |     | 155 |     |     |     |     | 160 |
| Leu | Ala | Leu | His | Val | Phe | Leu | Asn | Gly | Leu | Ser | Leu | Lys | Gly | Arg | Asn |
|     |     |     |     | 165 |     |     |     |     | 170 |     |     |     |     | 175 |     |
| Lys | Lys | Asp | Val | Cys | Met | Ser | Leu | Asn | His | Asn | Tyr | Ile | Ser | Ser | Val |
|     |     |     | 180 |     |     |     |     | 185 |     |     |     |     | 190 |     |     |

-continued

```
Ser Glu Asn Phe Pro Arg Gly Lys Arg Gly Leu Thr Gly Leu Tyr Leu
        195                 200                 205
Gln His Glu Gln Lys Val Thr Ala Ala Tyr Arg Arg Ile Tyr Gly Gly
    210                 215                 220
Ser Thr Thr Thr Ala Phe Trp Tyr Val Ser Lys Phe Gly Pro Asp Glu
225                 230                 235                 240
Lys Ser Leu Val Leu Ala Leu Arg Tyr Tyr Leu Leu Gln Ala Gln Glu
                245                 250                 255
Glu Val Thr Gly Ile Ala Thr Gly Tyr Asp Leu Gln Ala Ile Lys Asp
            260                 265                 270
Ile Cys Lys Thr Tyr Ala Val Ser Val Asn Pro Asn Pro Thr Gly Phe
        275                 280                 285
Leu Ala Ala Asp Leu Thr Ser Phe Ser Arg Leu Ser Arg Phe Cys Cys
    290                 295                 300
Leu Ser Tyr Tyr Ser Lys Gly Ser Val Ala Ile Ala Phe Pro Ser Tyr
305                 310                 315                 320
Val Glu Arg Arg Ile Met Ala Asp Ile Ala Glu Val Asp Ala Leu Arg
                325                 330                 335
Glu Tyr Ile Glu Arg Asp Arg Pro Ser Leu Lys Ile Ser Asp Leu Glu
            340                 345                 350
Phe Val Lys Tyr Ile Tyr Leu Ala Tyr Phe Glu Cys Tyr Asn Arg Glu
        355                 360                 365
Gln Leu Lys Arg His Leu Lys Asp Val Thr Val Ser Leu Pro Asp Glu
    370                 375                 380
Asp Ile Tyr Lys Lys Ser Ser Leu Gly Lys Cys Ala Val Glu Asn Phe
385                 390                 395                 400
    Phe Thr His Val Arg Ser Arg Leu Asn Val Asn Asp His Ile Ala His
                    405                 410                 415
Asn Val Leu Pro Glu Gln Val Glu Met Gly Asn Lys Leu Val Arg Lys
            420                 425                 430
Phe Gly Arg Ala Arg Met Tyr Leu Ser Thr Thr Met Thr Asn Glu Ser
        435                 440                 445
His Phe Thr Gly Ile Cys Glu Cys Ala Ser Val Ile Leu Lys Arg Leu
    450                 455                 460
Asp Thr Leu Glu Met Lys Leu Gln Lys Tyr Gly Trp Pro Ser Asp Arg
465                 470                 475                 480
Val Asp Gly Ser Asn Leu Met Ala Asp Asn Gln Asn Asn Ser Thr Leu
            485                 490                 495
Ile Pro Tyr Asp Lys Ser Arg Ser Ser Gly Met Ile Leu Glu Cys Ser
        500                 505                 510
Asn Thr His Ser Arg Gly Gly Pro Met Ile Val Lys Arg Leu Leu Ala
    515                 520                 525
Leu Val Ser Ala Asp Ser Arg Ala Gly Gly Ile Gly Pro Ala Asn Met
530                 535                 540
Leu Met Gly Ile Asp Ser Ala Ile Asp Gly Pro Leu Pro Val Tyr Arg
545                 550                 555                 560
Val Gly Met Ser Lys Gly Arg Gln Ala Phe Thr Val Leu Met Thr Glu
            565                 570                 575
Cys Trp Glu Arg Thr Ile Pro Ser Pro Gly Ser Ala Lys Ala His Leu
        580                 585                 590
Ile Lys Leu Asn Asn Ser Tyr Gly Thr Ser Thr Glu Asp Leu Ile Ser
    595                 600                 605
Arg Asp Leu Phe Leu Thr Ser Glu Ile Glu Gln Leu Ile Gly Ser Thr
610                 615                 620
```

-continued

| | | | | | | | | | | | | | | |
|---|---|---|---|---|---|---|---|---|---|---|---|---|---|---|
| Val | Glu | Leu | Pro | Glu | Ile | Thr | Cys | Gly | Ser | Ala | Asp | Glu | Gln | Gln | Tyr |
| 625 | | | | 630 | | | | 635 | | | | | | 640 |
| Ile | Asn | Arg | Asn | Glu | Val | Phe | Asn | Gly | Asn | Leu | Ala | Ile | Gly | Asn | Ile |
| | | | | 645 | | | | 650 | | | | | 655 | | |
| Val | Leu | Asp | Val | Asp | Ile | His | Leu | Arg | Asn | Pro | Ile | Pro | Leu | Arg | Leu |
| | | | 660 | | | | | 665 | | | | 670 | | | |
| Met | His | Ala | Ala | Ile | Arg | Gly | Phe | Arg | Ser | Gly | Ile | Leu | Arg | Ala | Leu |
| | | 675 | | | | 680 | | | | | 685 | | | | |
| Ala | Leu | Leu | Leu | Pro | Lys | Ala | Asn | Ile | Asp | His | Gly | Ser | Tyr | Pro | Cys |
| 690 | | | | | 695 | | | | | 700 | | | | | |
| Tyr | Phe | Tyr | Lys | Ser | Ser | Cys | Lys | Lys | Ser | Arg | Val | Met | Gly | Gly | Ala |
| 705 | | | | | 710 | | | | 715 | | | | | | 720 |
| Pro | Trp | Met | Leu | His | Asp | Ala | Glu | Leu | Ala | Pro | Asp | Tyr | Ser | Met | Phe |
| | | | | 725 | | | | 730 | | | | | | 735 | |
| Glu | Asn | Ala | Glu | Phe | Asp | Leu | Glu | Met | Gly | Ile | Asp | Asp | Pro | Leu | Leu |
| | | | 740 | | | | | 745 | | | | | 750 | | |
| Ile | Asp | Gln | Ile | Asp | Glu | Ser | Leu | Thr | Arg | Trp | Ser | Ser | Glu | Ser | Ser |
| | | 755 | | | | 760 | | | | | 765 | | | | |
| Arg | Ser | Val | Asp | Leu | Asp | Pro | Asp | Lys | Pro | Cys | Gly | Cys | His | Asp | Lys |
| 770 | | | | | 775 | | | | | 780 | | | | | |
| Ile | Gly | Leu | Arg | Val | Cys | Ile | Pro | Val | Pro | Ser | Pro | Tyr | Leu | Leu | Val |
| 785 | | | | | 790 | | | | 795 | | | | | | 800 |
| Gly | Ser | Lys | Thr | Leu | Ala | Gly | Leu | Ser | Arg | Ile | Ile | Gln | Gln | Ala | Val |
| | | | | 805 | | | | 810 | | | | | | 815 | |
| Leu | Leu | Glu | Arg | Asn | Phe | Val | Glu | Thr | Ile | Gly | Pro | Tyr | Leu | Lys | Asn |
| | | | 820 | | | | | 825 | | | | | 830 | | |
| Tyr | Glu | Ile | Ile | Asp | Ser | Gly | Val | Tyr | Gly | His | Gly | Arg | Ser | Leu | Arg |
| | | 835 | | | | | 840 | | | | | 845 | | | |
| Leu | Pro | Phe | Phe | Gly | Lys | Ile | Asp | Glu | Asn | Gly | Ile | Val | Ser | Arg | Arg |
| 850 | | | | | 855 | | | | | 860 | | | | | |
| Leu | Val | Pro | Phe | Phe | Val | Ile | Pro | Asp | Asp | Cys | Ala | Asp | Met | Glu | Lys |
| 865 | | | | | 870 | | | | | 875 | | | | | 880 |
| Phe | Ile | Val | Ala | His | Phe | Glu | Pro | Lys | Asn | Phe | His | Phe | His | Ser | Ser |
| | | | | 885 | | | | 890 | | | | | 895 | | |
| Ile | Pro | Leu | Glu | Lys | Ala | Ala | Ile | Ile | Leu | Lys | Asp | Ile | Gly | Gly | Glu |
| | | | | 900 | | | | 905 | | | | | 910 | | |
| Tyr | Ala | Gly | Phe | Phe | Glu | Arg | Lys | Ile | Thr | Val | Asn | Arg | Asp | Ile | Phe |
| | | 915 | | | | | 920 | | | | | 925 | | | |
| Phe | Gly | Thr | Arg | Leu | Ser | Leu | Ser | Ile | Ala | Leu | Arg | Glu | Arg | Gly | Val |
| | | 930 | | | | 935 | | | | | 940 | | | | |
| Asp | Ile | Asn | Asp | Cys | Ala | Ala | Ile | Thr | Thr | Phe | Val | Thr | Asp | His | Ile |
| 945 | | | | | 950 | | | | | 955 | | | | | 960 |
| Leu | Asp | Asp | Ile | Ile | Thr | Tyr | Val | Tyr | Glu | His | Ile | Pro | Asp | His | Ala |
| | | | | 965 | | | | 970 | | | | | 975 | | |
| Ile | Glu | Tyr | Gln | Asn | Leu | Ser | Val | Ser | Cys | Cys | Val | Val | Lys | Ser | Asp |
| | | | 980 | | | | | 985 | | | | | 990 | | |
| Trp | Ile | Leu | Leu | Gln | Leu | Ile | Pro | Asn | Lys | Thr | Ile | Gly | Tyr | Arg | His |
| | | | 995 | | | | | 1000 | | | | | 1005 | | |
| Gly | Phe | Thr | Cys | Val | Arg | Phe | Lys | His | Ala | Arg | Ala | Arg | Arg | Ala | Ser |
| | 1010 | | | | | 1015 | | | | | 1020 | | | | |
| Ala | Arg | Ser | Tyr | Leu | Ala | Leu | Asn | Val | Asp | Ala | His | Gly | Arg | Leu | Cys |
| 1025 | | | | | 1030 | | | | | 1035 | | | | | 1040 |
| Val | Cys | Val | Ile | Gln | Gln | Cys | Phe | Ala | Ala | Lys | Cys | Gly | Asn | Asn | Lys |
| | | | | 1045 | | | | | 1050 | | | | | 1055 | |
| Leu | Arg | Thr | Leu | Phe | Thr | Val | Asp | Ile | Asp | Ser | Lys | Cys | Arg | Leu | Glu |

-continued

| | | |
|---|---|---|
| 1060 | 1065 | 1070 |

His Gln
1074

MAREKS' DISEASE VIRUS VACCINE

This is a continuation of application Ser. No. 07/615,211 filed Nov. 16, 1990, now abandoned.

BACKGROUND OF THE INVENTION

The present invention is concerned with a nucleic acid sequence encoding a Marek's Disease virus polypeptide, a recombinant nucleic acid molecule comprising such a nucleic acid sequence, a vector virus comprising said nucleic acid sequence, a host cell transformed with such a nucleic acid sequence, a Marek's Disease virus polypeptide and antibodies reactive therewith, as well as a vaccine against Marek's Disease.

Marek's Disease (MD) is a malignant, lymphoproliferative disorder of domestic fowl caused by a herpesvirus: Marek's Disease Virus (MDV). MD is ubiquitous, occurring in poultry-producing countries throughout the world. Chickens raised under intensive production systems will inevitably suffer losses from MD. MD affects chickens from about 6 weeks of age, occurring most frequently between ages of 12 and 24 weeks.

Three forms of MD are recognized clinically, classical MD, acute MD and transient paralysis.

Classical MD is characterized by peripheral nerve enlargement caused by lymphoid infiltration and demyelination, and paralysis is the dominant clinical sign. Mortality is variable but normally under 10-15 percent.

In the acute form there are multiple and diffuse lymphomatous tumors in the visceral organs. Mortality from this form of MD is usually higher than from the classical form. An incidence of 10-30 percent is common in unvaccinated flocks and outbreaks involving up to 70% of the flock may be encountered. The pathological lesions in both classical and acute MD are essentially similar, involving the proliferation and infiltration of malignantly transformed T-lymphoblasts into normal tissues, peripheral nerves in the case of the classical form and visceral organs in the case of the acute form.

Furthermore, the MDV has been shown to be responsible for encephalitis of young chickens characterized by sudden paralysis.

Serological classification of MD related viruses yielded three serotypes:

| | |
|---|---|
| Type I | naturally occurring virulent strains of Marek's disease virus which are pathogenic and tumorigenic to chickens, and attenuated nonpathogenic strains derived therefrom |
| Type II | naturally occurring nonpathogenic strains of Marek's disease virus; and |
| Type III | herpesvirus of turkeys ("HVT"), which is nonpathogenic to chickens. |

Serial passage of pathogenic strains of MDV serotype I was found to result in loss of pathogenicity and oncogenicity, but not of immunogenicity. Attenuated strains derived from HPRS-16 and CVI-988 strains have been applied as vaccines. SB-I and HN-I MDV strains (serotype 2) have also been shown to be useful in vaccination. HVT, first isolated from turkeys, is apathogenic in turkeys and domestic fowls, antigenically related to serotype 1 and 2 MD viruses and extensively used as a vaccine against MD.

There are no methods of treatment of MD and control is based on management methods which isolate growing chickens from sources of infection, the use of genetically resistant stock, and vaccination. However, management procedures are normally not cost-effective and the progress has been disappointing with respect to the selection of poultry stock with increased genetically controlled resistance. Nowadays, control of MD is almost entirely based on vaccination.

Current vaccines comprise chemically inactivated virus vaccines or modified live-virus vaccines. However, inactivated vaccines require additional immunizations, disadvantageously contain adjuvants, are expensive to produce and are laborious to administer. Further, some infectious virus particles may survive the inactivation process and may cause disease after administration to the animal.

In general, attenuated live virus vaccines are preferred because they evoke an immune response often based on both humoral and cellular reactions. Up to now, such vaccines based on MDV serotype I strains could only be prepared by serial passage of virulent strains in tissue culture. However, because of this treatment uncontrolled mutations are introduced into the viral genome, resulting in a population of virus particles heterogeneous with regard to virulence and immunizing properties. Overattenuation during passage in cell culture can also be a problem with these vaccines. One must achieve a delicate balance between ensuring that the vaccine is not virulent while making certain that it is still protective. In addition it is well known that such traditional attenuated live virus vaccines can revert to virulence resulting in disease outbreaks in inoculated animals and the possible spread of the pathogen to other animals. The occurrence of very virulent field strains of MD virus against which live HVT vaccines provided poor protection have now been isolated and are responsible for excessive losses in various parts of the world. Bivalent vaccines consisting of serotype 2 and serotype 3 strains are reasonably effective against very virulent field isolates in some cases. Multivalent vaccines containing serotype antigens should be even more effective at eliciting immunity against these very virulent strains.

Improved vaccines might be constructed based on recombinant DNA technology. These vaccines would only contain the necessary and relevant MDV immunogenic material which is capable of eliciting a protective immune response against the MDV pathogens, or the genetic information encoding said material, and would not display above mentioned disadvantages of the live or inactivated vaccines.

SUMMARY OF THE INVENTION

According to the present invention a nucleic acid sequence encoding a MDV polypeptide is provided which can be applied for the preparation of a vaccine for the immunization of poultry against MD.

"Nucleic acid sequence" as used herein refers to a polymeric form of nucleotides of any length, both to ribonucleic acid sequences and to deoxyribonucleic acid sequences. In principle, this term refers to the primary structure of the molecule. Thus, this term includes double and single stranded DNA, as well as double and single stranded RNA, and modifications thereof.

In general, the term "polypeptide" refers to a molecular chain of amino acids with a biological activity and does not refer to a specific length of the product. If required the polypeptide can be modified in vivo or in vitro, for example by glycosylation, amidation, carboxylation or phosphorylation; thus inter alia, peptides, oligopeptides and proteins are included.

According to the invention a nucleic acid sequence containing a gene encoding the MDV polypeptide MD18 or MD20, respectively, have been isolated and characterized and were found to be recognized by the immune system of the host. The genes encoding said polypeptides were identified by screening bacteriophage expression libraries made in the lambda gt11 vector, with polyvalent sera from chickens infected with a virulent MD virus strain.

The gene encoding the MD18 polypeptide maps to the unique long ($U_L$) region of the MDV genome and encodes a polypeptide of about 663 amino acids in length. The amino acid sequence of the polypeptide encoded by the MD18 gene is shown in SEQ ID NO: 2.

The gene encoding the MD20 polypeptide also maps to the $U_L$ region of the MDV genome and encodes a polypeptide of about 1074 amino acids in length. The amino acid sequence of the polypeptide encoded by the MD20 gene is shown in SEQ ID NO: 4.

More particularly, this invention provides a nucleic acid sequence that encodes the MD18 polypeptide or MD20 polypeptide having an amino acid sequence shown in SEQ ID NO: 2 or SEQ ID NO: 4, respectively.

Also included within the scope of the present invention are nucleic acid sequences encoding a functional equivalent of said MD18 or MD20 polypeptide having corresponding immunological characteristics.

It will be understood that for the particular MD18 or MD20 polypeptide embraced herein, derived from the serotype 1 GA strain, natural variations can exist between individual viruses or strains of MDV of Type 1. These variations may be demonstrated by (an) amino acid difference(s) in the overall sequence or by deletions, substitutions, insertions, inversions or additions of (an) amino acid(s) in said sequence. Amino acid substitutions can be expected which can be expected probably do not essentially alter biological and immunological activities have been described. Amino acid replacements between related amino acids or replacements which have occurred frequently in evolution are, for example Ser/Ala, Ser/Gly, Asp/Gly, Asp/Asn, Ile/-Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the similarity between homologous polypeptides. Nucleic acid sequences encoding such functional equivalents are included within the scope of this invention. Moreover, the potential exists to use recombinant DNA technology for the preparation of nucleic acid sequences encoding these various functional equivalents.

Preferably, nucleic acid sequences according to the invention may be derived from available isolates of MDV of Type 1, strains such as GA, JM, HPRS-16, Conn A, RB-IB CVI-988 or Md 11, the GA strain being the most preferred strain.

In addition nucleic acid sequences encoding the MD18 polypeptide or MD20 polypeptide or variations thereof as mentioned above may also be derived from MDV strains belonging to Type 2 or Type 3, e.g. HN, HPRS-24, SB-1 or FC126.

DETAILED DESCRIPTION OF THE INVENTION

The information provided in SEQ ID NO: 1–4 allows a person skilled in the art to isolate and identify the nucleic acid sequences encoding the variant functional equivalent polypeptides mentioned above having corresponding immunological characteristics with the MD18 or MD20 polypeptide disclosed herein. The generally known blotting and hybridization techniques can be used for that purpose (Experiments in Molecular Biology, ed. R. J. Slater, Clifton, U.S.A., 1986; Singer-Sam, J. et al., Proc. Natl. Acad. Sci. 80, 802–806, 1983; Maniatis, T. et al., in Molecular Cloning, A laboratory Manual, Cold Spring Harbor Laboratory Press, U.S.A., 1989). For example, restriction enzyme digested DNA fragments derived from a specific MDV strain is electrophoresed and transferred, or "blotted" thereafter onto a piece of nitrocellulose filter. It is now possible to identify the nucleic sequences encoding the functional equivalent polypeptides on the filter by hybridization to a defined labelled DNA or "probe" back translated from the amino acid sequence shown in SEQ ID NO: 2 or SEQ ID NO: 4, under specific conditions of salt concentration and temperature that allow hybridization of the probe to any homologous DNA sequences present on the filter. After washing the filter, hybridized material may be detected by autoradiography. From an agarose gel with starting DNA that was not blotted, DNA can now be obtained that encodes a polypeptide functionally equivalent to a polypeptide disclosed in SEQ ID NO: 2 or 4.

In another way, DNA obtained from a specific MDV strain may be cloned into a λgt11 phage and expressed into a bacterial host. Recombinant phages can then be screened with polyclonal serum raised against the purified MD18 or MD20 polypeptide, determining the corresponding immunological characteristic of the variant polypeptide. The above mentioned procedure is outlined in detail in Example 1. The production of the polyclonal serum elicited against MD18 or MD20 is described below.

As is well known in the art, the degeneracy of the genetic code permits substitution of bases in a codon resulting in another codon but still coding for the same amino acid, e.g. the codon for the amino acid glutamic acid is both GAT and GAA. Consequently, it is clear that for the expression of a polypeptide with the amino acid sequence shown in SEQ ID NO: 2 or SEQ ID NO: 4 use can be made of a derivate nucleic acid sequence (functional equivalent) with such an alternative codon composition different from the nucleic acid sequence shown in said SEQ ID's.

A preferred nucleic acid sequence according to the invention is characterized in that said sequence contains the deoxyribonucleic acid sequence shown in SEQ ID NO: 1 or SEQ ID NO: 3.

Furthermore, also fragments of the nucleic acid sequences encoding the MD18 or MD20 polypeptide or functional equivalents thereof as mentioned above are included in the present invention.

The term "fragment" as used herein means a DNA or amino acid sequence comprising a subsequence of one of the nucleic acid sequences or polypeptides of the invention. Said fragment is or encodes a polypeptide having one or more immunoreactive and/or antigenic determinants of a MDV polypeptide, i.e. has one or more epitopes which are capable of eliciting an immune response in a chicken and/or is capable of specifically binding to a complementary antibody. Methods for determining usable polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments introduced in a suitable host cell environment.

All modifications resulting in such functional equivalents of the MD18 or MD20 polypeptide are included within the scope of the present invention for as long as the immunological characteristics of the MD18 or MD20 polypeptide remain unaffected in essence.

A nucleic acid sequence according to the present invention can be ligated to various replication effecting DNA sequences with which it is not associated or linked in nature, optionally containing portions of DNA encoding fusion protein sequences such as $\beta$-galactosidase, resulting in a so-called recombinant nucleic acid molecule which can be used for the transformation of a suitable host. Such hybrid DNA molecules are preferably derived from, for example plasmids, or from nucleic acid sequences present in bacteriophages, cosmids or viruses. Specific vectors which can be used to clone nucleic acid sequences according to the invention are known in the art and include plasmid vectors such as pBR322, the various pUC, pGEM and Bluescript plasmids, bacteriophages, e.g. $\lambda$gt-Wes-$\lambda$ B, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1-24, 1990). The methods to be used for the construction of a recombinant nucleic acid molecule according to the invention are known to those of ordinary skill in the art and are inter alia set forth in Maniatis, T. et al. (ibid, 1989). For example, the insertion of the nucleic acid sequence according to the invention into a cloning vector can easily be achieved by ligation with an enzyme such as T4 DNA ligase when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the recessive termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of a heterologous nucleic acid sequence into a host cell, irrespective of the method used, for example, by direct uptake or transduction. The heterologous nucleic acid sequence may be maintained through autonomous replication or alternatively may be integrated into the host genome. If desired, the recombinant DNA molecules are provided with appropriate control sequences compatible with the designated host which can regulate the expression of the inserted nucleic acid sequence.

The recombinant nucleic acid molecule according to the invention preferably contains one or more marker activities that may be used to select for desired transformants, such as ampicillin and tetracycline resistance in pBR322, ampicillin resistance and $\beta$-galactosidase activity in pUC8.

A suitable host cell is a cell which can be transformed by a nucleic acid sequence encoding a polypeptide or by a vector virus or a recombinant nucleic acid molecule comprising such a nucleic acid sequence and which can if desired be used to express said polypeptide encoded by said nucleic acid sequence. The host cell can be of procaryotic origin, e.g. bacteria such as *Escherichia coli, Bacillus subtilis* and Pseudomonas species; or of eucaryotic origin such as yeast, e.g. *Saccharomyces cerevisiae* or higher eucaryotic cells such as insect, plant or mammalian cells, including HeLa cells and Chinese hamster ovary (CHO) cells. Insect cells include the Sf9 or Sf21 cell line of Spodoptera frugiperda (Luckow et al., Biotechnology 6, 47-55, 1989). Information with respect to the cloning and expression of the nucleic acid sequence of the present invention in eucaryotic cloning systems can be found in Esser, K. et al. (Plasmids of Eukaryotes, Springer-Verlag, 1986).

In general, prokaryotes are preferred for cloning and manipulation of DNA sequences and for constructing the vectors useful in the invention. For example *E. coli* K12 is particularly useful. Other microbial strains which may be used include *E. coli* strains such as DH5$\alpha$, JM101 or HB101.

For expression, nucleic acid sequences of the present invention are operably linked to expression control sequences. Such control sequences may comprise promoters, enhancers, operators, inducers, ribosome binding sites etc.

When the host cells are bacteria, illustrative useful expression control sequences include the Trp promoter and operator (Goeddel, et al., Nucl. Acids Res. 8, 4057, 1980); the lac promoter and operator (Chang, et al., Nature 275, 615, 1978); the outer membrane protein (OMP) promoter (Nakamura, K. and Inouge, M., EMBO J. 1, 771-775, 1982); the bacteriophage $\lambda$ promoters and operators (Remaut, E. et al., Nucl. Acids Res. 11, 4677-4688, 1983); the $\alpha$-amylase (*B. subtilis*) promoter and operator, termination sequence and other expression enhancement and control sequences compatible with the selected host cell. When the host cell is yeast, illustrative useful expression control sequences include, e.g., $\alpha$-mating factor. For insect cells the polyhedrin or p10 promoters of baculoviruses can be used (Smith, G. E. et al., Mol. Cell. Biol. 3, 2156-65, 1983). When the host cell is of mammalian origin illustrative useful expression control sequences include, e.g., the SV-40 promoter (Berman, P. W. et al., Science 222, 524-527, 1983) or, e.g. the metallothionein promoter (Brinster, R. L., Nature 296, 39-42, 1982) or a heat shock promoter (Voellmy et al., Proc. Natl. Acad. Sci. USA 82, 4949-53, 1985). Alternatively, also expression control sequences present in MDV, in particular those regulating the expression of MD18 or MD20 may be applied. For maximizing gene expression, see also Roberts and Lauer (Methods in Enzymology 68, 473, 1979).

The present invention also comprises a polypeptide displaying MDV immunological characteristics containing at least part of the MD18 or MD20 amino acid sequence shown in SEQ ID NO: 2 or SEQ ID NO: 4, respectively, or derivatives thereof, essentially free from the whole virus or other proteins with which it is ordinarily associated.

It will be understood that derivatives of said amino acid sequences displaying the same immunological properties in essence, i.e. immunological equivalents, are also within the scope of the present invention.

Immunological equivalents of the MD18 or MD20 polypeptide disclosed herein are the corresponding polypeptides present in viruses of other strains of MD Type 1 or in viruses of strains belonging to Type 2 or 3. Said equivalents can be produced through the expression of the genes encoding said equivalents, the genes being identified and isolated making use of the information provided herein as described above.

In addition a polypeptide comprising a fragment of the MD18 or MD20 polypeptide or functional equivalent thereof, which can be used for immunization of poultry against MD is included in the present invention. Various methods are known for detecting such usable polypeptide fragments within a known amino acid sequence.

Suitable immunochemically active polypeptide fragments of a polypeptide according to the invention containing (an) epitope(s) can be found by means of the method described in Patent Application WO 86/06487, Geysen, H. M. et al. (Prod. Natl. Acad. Sci. 81, 3998–4002, 1984), Geysen, H. M. et al. (J. Immunol. Meth. 102, 259–274, 1987) based on the so-called pepscan method, wherein a series of partially overlapping polypeptides corresponding with partial sequences of the complete polypeptide under consideration, are synthesized and their reactivity with antibodies is investigated.

In addition, a number of regions of the polypeptide, with the stated amino acid sequence, can be designated epitopes on the basis of theoretical considerations and structural agreement with epitopes which are now known.

The determination of these regions was based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds with the aid of Berzofsky's amphiphilicity criterion (Science 235, 1059–62, 1987).

Such epitopes can also be generated experimentally by limited exposure of the polypeptide to the proteolytic activity of Cathepsin D. Cleavage of a protein antigen by this enzyme specifically recognizes amino acid sequence patterns which are also found within the $NH_2$-terminal residues of peptides recognized by the major histocompability complex on the surface of antigen-presenting cells (v. Noort, J. M. and v.d. Drift, A. C. M., J. Biol. Chem. 264, 14159, 1989).

In another embodiment of the invention a polypeptide having an amino acid sequence encoded by a nucleic acid sequence mentioned above is used.

Immunization of poultry against MDV infection can, for example be achieved by administering to the animals a polypeptide according to the invention in an immunologically relevant context as a so-called subunit vaccine. The subunit vaccine according to the invention may comprise a polypeptide in a pure form, optionally in the presence of a pharmaceutically acceptable carrier. The polypeptide can optionally be covalently bonded to a non-related protein, which, for example can be of advantage in the purification of the fusion product. Examples are β-galactosidase, protein A, prochymosine, blood clotting factor Xa, etc.

In some cases the ability to raise neutralizing antibodies against these polypeptides per se may be low. Small fragments are preferably conjugated to carrier molecules in order to increase their immunogenicity. Suitable carriers for this purpose are macromolecules, such as natural polymers (proteins like keyhole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

Polypeptides to be used in such subunit vaccines can be prepared by methods known in the art, e.g. by isolating said polypeptides from MDV, by recombinant DNA techniques or by chemical synthesis.

If required the polypeptides according to the invention to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a microorganism (e.g. a bacterium or virus) in such a way that the recombinant microorganism is still able to replicate thereby expressing a polypeptide coded by the inserted nucleic acid sequence.

For example the technique of in vivo homologous recombination can be used to introduce a heterologous nucleic acid sequence, e.g. a nucleic acid sequence according to the invention into the genome of the vector microorganism.

First, a DNA fragment corresponding with an insertion region of the vector genome, i.e. a region which can be used for the incorporation of a heterologous sequence without disrupting essential functions of the vector such as those necessary for infection or replication, is inserted into a cloning vector according to standard recDNA techniques. Insertion regions have been reported for a large number of microorganisms (e.g. EP 80,806, Ep 110,385, EP 83,286, EP 3-14,569, WO 88/02022 and WO 88/07088).

Second, if desired, a deletion can be introduced into the insertion region present in the recombinant DNA molecule obtained from the first step. This can be achieved for example by appropriate exonuclease III digestion or restriction enzyme treatment of the recombinant DNA molecule from the first step.

Third, the heterologous nucleic acid sequence is inserted into the insertion region present in the recombinant DNA molecule of the first step or in place of the DNA deleted from said recombinant DNA molecule. The insertion region DNA sequence should be of appropriate length as to allow homologous recombination with the vector genome to occur. Thereafter, suitable cells can be transformed with vector genomic DNA in the presence of the recombinant DNA molecule containing the insertion flanked by appropriate vector DNA sequences whereby recombination occurs between the corresponding regions in the recombinant DNA molecule and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant microorganism can be administered to the host animal for immunization whereafter it is maintained and optionally replicates in the body of the inoculated animal, expressing in vivo a polypeptide coded for by the nucleic acid sequence according to the invention inserted in a vector organism and resulting in the stimulation of the immune system of the inoculated animal.

Suitable vectors for the incorporation of a nucleic acid sequence according to the invention can be derived from viruses such as (avian) pox viruses, e.g. vaccinia virus or fowl pox virus (EP 314,569 and WO 88/02022), herpes viruses such as HVT (WO 88/07088), adeno virus or influenza virus, or bacteria such as E. coli or specific Salmonella species. With recombinant microorganisms of this type, the polypeptide synthesized in the host cell can be exposed as a surface antigen. In this context fusion of the said polypeptide with OMP proteins, or pilus proteins of for example E. coli or with synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will be expressed, generating protection against various pathogens and/or against various antigens of a given pathogen.

A vaccine according to the invention can be prepared by culturing a host cell infected with a vector virus comprising a nucleic acid sequence according to the invention, whereafter virus containing cells and/or vector viruses grown in the cells can be collected, optionally in a pure form, and formed to a vaccine optionally in a lyophilized form.

Above mentioned host cells comprising a nucleic acid sequence according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells containing a nucleic acid sequence according to the invention are cultured in an adequate volume and the polypeptides produced are isolated from such cells or from the medium if the protein is secreted. Polypeptides secreted into the medium can be isolated and purified by standard techniques, e.g. salt fractionation, centrifugation, ultrafiltration, chromatography, gel filtration or immuno affinity chromatography, whereas intracellular polypeptides can be isolated by first collecting said cells, disrupting the cells, for example by sonication or by other mechanically disruptive means such as French press followed by separation of the polypeptides from the other intracellular components and forming the polypeptides to a vaccine. Cell disruption could also be accomplished by chemical (e.g. EDTA treatment) or enzymatic means such as lysozyme digestion.

Antibodies or antiserum directed against a polypeptide according to the invention have potential uses in passive immunotherapy, diagnostic immunoassays and generation of anti-idiotype antibodies.

The MDV polypeptides MD18 or MD20 as described above can be used to produce antibodies, both polyclonal, monospecific and monoclonal. If polyclonal antibodies are desired, techniques for producing and processing polyclonal sera are known in the art (e.g. Mayer and Walter, eds, Immunochemical Methods in Cell and Molecular Biology, Academic Press, London, 1987). In short, a selected mammal, e.g. rabbit is given (multiple) injections with one of the above mentioned immunogens, about 20 $\mu$g to about 80 $\mu$g of protein per immunization. Immunizations are given with an acceptable adjuvant, generally equal volumes of immunogen and adjuvant. Acceptable adjuvants include Freund's complete, Freund's incomplete, alum-precipitate or water-in-oil emulsions, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art.

Monospecific antibodies to each of the immunogens are prepared by immunizing rabbits as described above with the purified proteins and thereafter affinity purified from polyspecific antisera by a modification of the method of Hall et al. (Nature 311, 379-387 1984). Monospecific antibody as used herein is defined as a single antibody species or multiple antibody species with homogeneous binding characteristics for the relevant antigen. Homogeneous binding as used herein refers to the ability of the antibody species to bind to a specific antigen or epitope.

Monoclonal antibodies reactive against each of the MDV immunogens can be prepared by immunizing inbred mice, preferably Balb/c with the appropriate protein. The mice are immunized intraperitoneally with about 100 ng to about 10 $\mu$g immunogen per 0.5 ml in an equal volume of a suitable adjuvant. Such acceptable adjuvants include Freund's complete, Freund's incomplete, alum-precipitate and water-in-oil emulsions. The mice are given intravenous booster immunizations of an equal amount of the immunogen without adjuvant at about days 14, 21 and 63 post primary immunization. At about day three after the final booster immunization, individual mice are serologically tested for anti-immunogen antibodies. Spleen cells from antibody producing mice are isolated and fused with murine myeloma cells, such as SP-2/0 or the like, by techniques known in the art (Kohler and Milstein, Nature 256; 495-497, 1975). Hybridoma cells are selected by growth in appropriate cell culture medium such as Dulbecco's modified Eagle's medium (DMEM) containing hypoxanthine, thymidine and aminopterin in an antibody producing hybridomas are cloned, preferably using the soft agar technique of MacPherson (Soft Agar Techniques, Tissue Culture Methods and Applications, Kruse and Paterson, eds., Academic Press, 276, 1973), Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific monoclonal antibodies are produced by cultivating the hybridomas in vitro or preparing ascites fluid in mice following hybridoma injection by procedures known in the art.

Anti-idiotype antibodies are immunoglobulins which carry an "internal image" of the antigen of the pathogen against which protection is desired and can be used as an immunogen in a vaccine (Dreesman et al., J. Infect. Disease 151, 761, 1985). Techniques for raising anti-idiotype antibodies are known in the art (MacNamara et al., Science 226, 1325, 1984).

The vaccine according to the invention can be administered in a conventional active immunization scheme: single or repeated administration in a manner compatible with the dosage formulation and in such amount as will be prophylactically and/or therapeutically effective and immunogenic. The administration of the vaccine can be done, e.g. intradermally, subcutaneously, intramusculary, intravenously or intranasally.

Additionally, the vaccine may also contain an aqueous medium or a water-containing suspension, often mixed with other constituents, e.g. in order to increase the activity and/or shelf life. These constituents may be salts, pH buffers, stabilizers (such as skimmed milk or casein hydrolysate), emulsifiers, adjuvants to improve the immune response (e.g. oils, muramyl dipeptide, aluminium-hydroxide, tocol derivatives, saponin, polyanions and amphipatic substances) and preservatives.

It is clear that a vaccine according to the invention may also contain immunogens related to other pathogens of poultry or may contain nucleic acid sequences encoding these immunogens, like antigens of Infectious Bronchitis Virus, Newcastle Disease virus Infectious Bursal Disease virus of Marek's Disease Virus different from those disclosed herein, to produce a multivalent vaccine.

The invention also relates to an "immunochemical reagent", which reagent comprises at least one of the polypeptides according to the invention or an antigenic fragment thereof.

The term "immunochemical reagent" signifies that the polypeptides according to the invention have been bound to a suitable support or have been provided with a labelling substance.

The supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of MDV related nucleic acids in any kind of tissue.

The present invention also provides a test kit comprising said nucleic acid sequence useful for the diagnosis of MDV infection.

The invention also relates to a test kit to be used in an immunoassay, this test kit containing at least one immunochemical reagent according to the invention.

The immunochemical reaction which takes place using this test kit is preferably a sandwich reaction, an agglutination reaction, a competition reaction or an inhibition reaction.

For carrying out a sandwich reaction, the test kit can consist, for example, of a polypeptide according to the invention bonded to a solid support, for example the inner wall of a microtest well, and either a labelled polypeptide according to the invention or a labelled anti-antibody.

EXAMPLE 1

Screening of Bacterial Expression Libraries with Convalescent Chicken Serum

The vector used for establishment of the library has been λgt11 (Young, R. A. and Davis, R. W. Proc. Natl. Acad. Sci. 80, 1194–1198, 1983). The genome of this expression vector contains a functional LacZ gene encoding the enzyme β-galactosidase with a unique EcoRI restriction site near the carboxy terminus. Insertion of DNA fragments from the MDV genome at this site, potentially results in the expression of a protein consisting of a MDV specific polypeptide fused to a major part of the β-galactosidase. Libraries representing a complex range of DNA fragments can be screened at high density for recombinant clones producing a fusion protein which is recognized by an antibody probe such as the serum from MDV infected birds. The library for these experiments was made using the DNA of a pool of BamHI plasmid clones which represented about 90% of the viral genome of MDV strain GA (Fukuchi et al., J. Virol. 51, 102, 1984). DNA from these plasmids was digested with BamHI, fragmented by sonication and size-selected by centrifugation on sucrose gradients. Fragments with a size between 0.5 and 4.0 kb were isolated, tailed with dG-residues and inserted by means of a synthetic adaptor into the unique EcoRI-site of the λgt10 vector (Le Bouc et al., FEBS lett. 196, 108, 1986; Huynh et al., in: Cloning Techniques, A Practical Approach, ed. Glover, D., 49–78, 1985) resulting in a library with an effective size of $5 \times 10^4$ pfu. Phages were amplified and purified on CsCl-gradients, DNA was extracted and inserts were recovered by restriction with EcoRI. Finally, these inserts were ligated into the EcoRI-site of the vector and recombinant phages were screened with chicken serum against MDV. This convalescent serum was obtained by infecting single-comb white leghorns (SPAFAS) with a virulent passage of the GA strain from MDV obtained from Dr. Calnek (Cornell University, NY, USA). Serum was collected over a 12 week period and samples were tested individually by indirect fluorescence for binding to MDV plaques in tissue cultures of chicken embryo fibroblasts (CEF).

Six of the sera were selected based on titer and specificity. A mixture of these samples was used in a 1:100 dilution to screen the λgt11 library on nitro-cellulose filters according to Young, R. A. et al. (Proc. Natl. Acad. Sci. U.S.A. 82, 2583, 1985). The second antibody for incubation of the filters was an alkaline phosphatase conjugated rabbit-anti-chicken serum (Sigma, St. Louis, USA) and positive signals were developed by the nitro blue tetrazolium/5-bromo-4-chloro-3-indolyl phosphate colour reaction (McGadey, Histochemie 23, 180, 1970). Series of candidates were selected and recombinants were plaque-purified until homogeneity. From four of these, the DNA insert in the λgt11 recombinant was recovered as a EcoRI fragment and transferred to the plasmid vector pUC8 (Vieira, J. and Messing, J., Gene 19. 259, 1982) or pGEM3Z (Promega, Madison, USA).

The resulting constructs were designated as pMD18, pMD20 and pMD21.

EXAMPLE 2

Cloning of the MD18 Gene and Structural Analysis of the Antigen MD18

The gene encoding the complete amino acid sequence of antigen MD18 was isolated by screening a λEMBL3 library representing the genome of MDV strain GA. The DNA used for establishment of this library was prepared by infecting chicken embryo fibroblasts (CEF) with a tissue culture adapted passage of MD strain GA provided by Dr. Nonoyama, Showa Univ., St. Petersburg, U.S.A. Cultures were incubated until 90% cytophatic effect (CPE) had developed and total DNA was prepared by proteinase K digestion and phenol/chloroform extraction. DNA was partially digested with Sau 3A (Promega, Madison, USA) and the size fraction of about 20 kb was isolated after separation in a 0.8% agarose gel. DNA fragments were ligated with BamHI/EcoRI digested λEMBL3 DNA (Promega., Madison, USA), packaged in vitro and plated on E.coli strain LE392. Screening of this library (Maniatis, T. et al., 1989, ibid) with the insert from pMD18 resulted among others in the isolation of λGA12 containing a 21 kb DNA mapped by restriction analysis to a region of the MDV viral genome about halfway the $U_L$ structural element. Within this 21 kb of DNA, the position of the sequence hybridizing with pMD18 was defined to a 3.8 kb BamHI fragment which was subcloned as such in both orientations using the vector pGEM3Z and resulting in the plasmids pMD41 and pMD42 respectively. Nucleotide sequence analysis in both orientations of the DNA was performed on progressively deleted subclones generated with the enzyme exonuclease III as described by Henikoff, S. (Gene 28, 357, 1984). After assemblage of all sequence data and translation of the sequence in the region of interest, a primary structure was deduced for the antigen originally identified in the immuno-screening by means of the convalescent chicken serum. The complete amino acid sequence of this antigen designated MD18, is presented in SEQ ID NO: 2.

EXAMPLE 3

Cloning of the MD20 Gene and Structural Analysis of the Antigen MD20

Analysis directly on the insert of pMD20 and pMD21 revealed a partially overlapping nucleotide sequence suggesting that both candidates were representing the same antigen.

The gene encoding the complete amino acid sequence of this antigen was isolated by screening a λEMBL3 library representing the genome of MDV strain GA. The DNA used for establishment of this library was prepared by infecting chicken embryo fibroblasts (CEF) with a tissue culture adapted passage of MD strain GA provided by Dr. Nonoyama, Showa Univ., St. Petersburg, U.S.A. Cultures were incubated until 90% cytophatic effect (CPE) had developed and total DNA was prepared by proteinase K digestion and phenol/chloroform extraction. DNA was partially digested with Sau 3A (Promega, Madison, USA) and the size fraction of about 20 kb was isolated after separation in a 0.8% agarose gel. DNA fragments were ligated with BamHI/EcoRI digested λEMBL3 DNA (Promega., Madison, USA), packaged in vitro and plated on E.coli strain LE392. Screening of this library (Maniatis, T. et al., 1982, ibid) with the insert from pMD21 resulted in the isolation of clone λGA09. This clone contained a 17 kb DNA insert that is located near the junction of the $U_L$ and $IR_L$ in the MDV viral genome. Referring to the restriction map as published by Fukuchi et al. (J. Virol. 51, 102, 1984), the 17 kb insert included the region in between the S and $I_2$ BamHI fragments. Restriction mapping on the DNA from λGA09 and hybridization with the insert from pMD21 identified the position of the gene in a 7.5 kb SalI fragment which was subcloned as such in pGEM3Z to result in pMD26. Nucleotide sequence analysis was performed on subclones generated by both the exonuclease III treatment (Henikoff, S., Gene 28, 257, 1984) and the use of convenient restriction sites. The final sequence obtained after assembling all data from the reactions done in both orientations was translated into the complete amino acid sequence of the antigen denominated MD20 and is shown in SEQ ID NO: 4.

EXAMPLE 4

Insertion of the Genes Encoding MDV Antigens MD=18 and MD20 into the Viral Genome of Herpes Virus of Turkey (HVT)

Based on the genome structure of HVT as published by Igarashi, T. et al. (Virology 157, 351, 1987) a region in the unique-short sequence element (Us) of the virus was selected for the insertion of foreign genes. The corresponding DNA fragment was screened from a λEMBL3 library constructed by partially digesting total DNA from HVT infected CEF following a procedure used previously for MDV strain GA. The insert of one of the λ-isolates, characterized by the absence of any BamHI restriction site, was denominated λHVT04 and analyzed in detail by physical mapping (FIG. 1). The sequence present in the 17.5 kb inserted fragment represented a major part of the Us region including part of the inverted repeat structure (Igarashi, T. et al., 1987, ibid). One of the 1.2 kb XhoI restriction fragments from λHVT04 was subcloned in pGEM3Z digested with Sal I resulting in plasmid pMD07 which contained a unique BglII site available for insertion of DNA fragments. The gene encoding antigen MD18 or MD20 was assembled from pMD41 and pMD26 respectively by removal of the excess of nucleotide sequences preceding the ATG-initiator and the creation of convenient restriction sites such as Sal I or XhoI flanking the coding region. For pMD41 this resulted in pMD46, and pMD26 gave pMD47, both restriction maps being presented in FIG. 2.

A strong promoter which could direct the expression of foreign genes after their insertion into the genome of the HVT virus was selected from the LTR sequence of Rous Sarcoma Virus (RSV). The promoter has been mapped on a 580 bp NdeI/HindIII restriction fragment from pRSVcat (Gorman et al., Proc. Natl. Acad. Sci. 79, 6777, 1982) and was inserted between the HindIII and PstI sites of pGEM3Z (Promega) by means of double stranded synthetic linkers on both sides of the fragment. The connection between the HindIII site from the vector pGEM3Z and the NdeI site of the RSV fragment carrying the LTR-promoter was made with a 30 bp linker containing cohesive ends compatible with HindIII on one and NdeI on the other site. However, after ligation both restriction sites are not restored due to deliberate, modifications in the outer nucleotides of the six base pair recognition sequence. In addition to the removal of these two sites, a new restriction site (BamHI) present within the linker itself was created at the corresponding position. A second 20 bp linker was synthesized which connected the HindIII site from the LTR fragment to the PstI site from pGEM3Z, in this case without destruction of the recognition sequence on either of the ends and adding the three convenient unique restriction sites BglII, XhoI and EcoRV, to those already present in the polylinker of pGEM3Z, e.g. PstI, SalI, XhoI and BamHI. The resulting derivative of pGEM3Z, designated pVEC01, therefore contains a 650 bp restriction fragment carrying the LTR promoter sequence immediately followed by seven restriction sites available for the insertion of foreign genes. The 650 bp fragment is flanked on either end by a BamHI restriction site and has been transferred as such to the unique BglII site present in the 1.2 kb HVT insert from pMD07. The cohesive ends generated by these two restriction enzymes are compatible but ligation does not restore either of the original recognition sequences for BglII or BamHI. One of the resulting constructs, carrying the LTR in the orientation towards the TRs, was designated pVEC04 and checked by restriction mapping (FIG. 3). The structure of this universal HVT recombination vector allows the insertion of foreign genes immediately downstream of the LTR promoter and subsequent integration of the complete expression cassette into the HVT genome by in vivo recombination. The positions of the different restriction sites downstream of the LTR in particular those for the enzymes BglII, XhoI and EcoRV are designed in such a way that even multiple gene insertion can be envisaged. A 2.5 kb SalI/XhoI restriction fragment derived from pMD46 carrying the MD18 gene, was inserted into the unique BglII site of pVEC04 downstream of the LTR promoter, resulting in pMD48. A 3.6 kb SalI restriction fragment derived from pMD47 carrying the MD20 gene was inserted into the unique XhoI site of pVEC04 downstream of the LTR promoter, resulting in pMD49.

DNA of the plasmids pMD48 or pMD49 was introduced together with total DNA prepared from HVT infected cells into CEF by a method based on the calcium phosphate DNA precipitation according to Graham, F. and v.d. Eb, A., (Virology 52, 456, 1973) with modifications described by Morgan et al. (Avian Diseases 34, 345, 1990). Two microgram of plasmid DNA from the constructs were mixed with 15 μg of DNA from HVT infected cells in a final volume of 560 μl $H_2O$ and added to 750 μl of HBSP (20 mM KCl, 560 mM NaCl, 24 mM glucose, 3 mM $Na_2HPO_4$, 100 mM HEPES, pH 7.0). Precipitates were formed by gradually adding 190 μl of 1M $CaCl_2$ solution and incubating the mixtures at room-temperature for 30 minutes. In the meantime, 15 ml of a suspension of secondary CEF from 10 day old embryos in medium 6/B8, for which the composition is based on Glasgow's modification of Eagle's Minimal Essential Medium supplemented with 2% of foetal calf serum, were seeded in φ 10 cm dishes at a density of $5 \times 10^5$ cells per ml. Calcium phosphate precipitated DNA was gently added to the cell suspension and dishes were incubated at 37° C. in a humified incubator containing 5% $CO_2$ in air. After 5 hours, medium was removed and 10 ml of solution containing equal volumes of HBSP and 30% glycerol was layered onto the cells. After a one to two minute incubation, the solution was removed, cells were washed with medium 6/B8 and dishes were incubated with fresh medium for 3 to 5 days until viral CPE developed. Detection of HVT recombinants expressing the MD18 or MD20 polypeptides was done by immunofluorescence staining using specific mono- or polyvalent sera against these MDV antigens.

Figure 1:
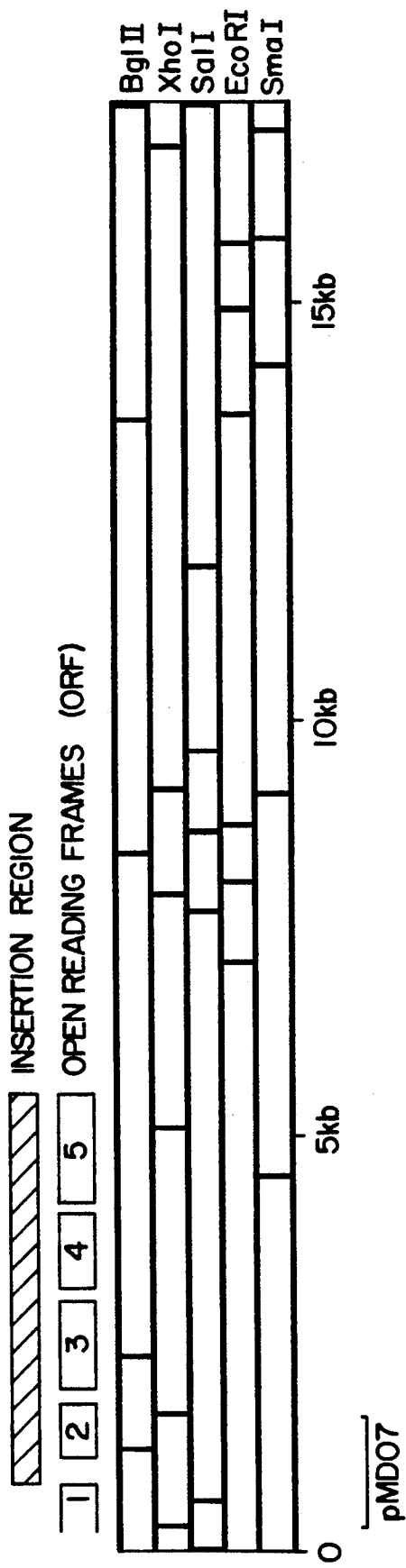
FIG. 1
Figure 3:
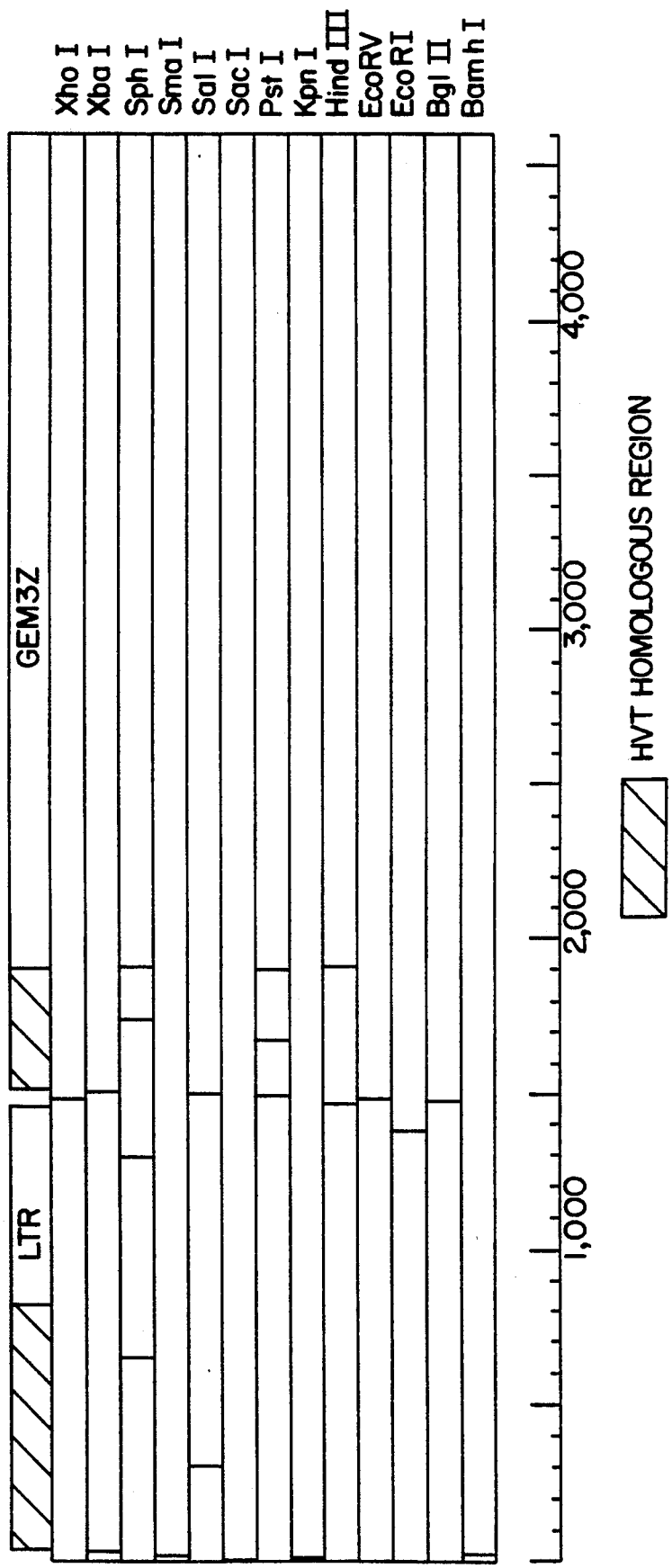

Restriction enzyme map of a DNA fragment essentially corresponding to the Us region of the HVT genome. The relative position of the insertion region consisting of four open reading frames and non-coding sequences in between is indicated.

FIG. 2

A. Restriction enzyme map of pMD46, containing the gene encoding MD18-antigen flanked by SalI and XhoI restriction sites. Vector plasmid was derived from pSP72 (Promega, Wisconsin, U.S.A.) by modification of the ClaI restriction site in the polylinker into SalI.

B. Restriction enzyme map of pMD47, containing the gene encoding MD20-antigen flanked by SalI restriction sites. Vector plasmid was derived from pSP72 (Promega, Wis., U.S.A.) by modification of the ClaI restriction site in the polylinker into SalI.

FIG. 3

Restriction enzyme map of pVEC04 showing the LTR-promoter inserted into the unique BglII site of the 1,2 kb XhoI HVT fragment from pMD07.

We claim:

1. An isolated and purified nucleic acid molecule encoding a Marek's disease virus polypeptide selected from the group consisting of:

a. MD18 having an amino acid sequence shown in SEQ ID NO:2, b. MD20 having an amino acid sequence shown in SEQ ID NO:4 and c. an antigenic fragment of MD18 on MD20.

2. An isolated and purified nucleic acid molecule which comprises a DNA sequence selected from the group consisting of SEQ ID:1, SEQ ID NO:3, and a DNA sequence encoding an antigenic fragment of SEQ ID NO:1 or SEQ ID NO:3.

3. A recombinant nucleic acid molecule according to claim 1, wherein the nucleic acid molecule is operably linked to an expression control sequence.

4. A recombinant nucleic acid molecule according to claim 2, wherein the DNA sequence is operably linked to an expression control sequence.

5. A host cell transformed with a nucleic acid molecule according to claim 1.

6. A host cell transformed with a nucleic acid sequence according to claim 2.

7. A viral vector comprising the nucleic acid molecule of claim 3.

8. A host cell transfected with the vector of claim 7.

9. A host cell transformed with a recombinant nucleic acid molecule according to claim 3.

10. A viral vector comprising the nucleic acid molecule of claim 4.

11. A host cell transfected with the vector of claim 10.

12. A vector comprising a nucleic acid molecule according to claim 1.

13. The vector of claim 12, wherein said vector is a virus.

14. A host cell containing a viral vector according to claim 13.

15. A vector comprising a nucleic acid molecule according to claim 2.

16. The vector of claim 15, wherein said vector is a virus.

17. A host cell containing a viral vector according to claim 16.

* * * * *